(12) United States Patent
Muller et al.

(10) Patent No.: US 12,349,980 B2
(45) Date of Patent: Jul. 8, 2025

(54) ALERTING AND MITIGATING DIVERGENCE OF ANATOMICAL FEATURE LOCATIONS FROM PRIOR IMAGES TO REAL-TIME INTERROGATION

(71) Applicant: Intuitive Surgical Operations, Inc., Sunnyvale, CA (US)

(72) Inventors: Leah Muller, San Francisco, CA (US); Paris A. Hajali, Jr., Tustin, CA (US); Hui Zhang, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 136 days.

(21) Appl. No.: 18/041,373

(22) PCT Filed: Jul. 27, 2021

(86) PCT No.: PCT/US2021/043317
§ 371 (c)(1),
(2) Date: Feb. 10, 2023

(87) PCT Pub. No.: WO2022/035584
PCT Pub. Date: Feb. 17, 2022

(65) Prior Publication Data
US 2023/0346479 A1 Nov. 2, 2023

Related U.S. Application Data

(60) Provisional application No. 63/065,420, filed on Aug. 13, 2020.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 34/30* (2016.02);
(Continued)

(58) Field of Classification Search
CPC .............. A61B 34/35; A61B 2034/105; A61B 2034/107; A61B 2034/2051;
(Continued)

(56) References Cited

U.S. PATENT DOCUMENTS 6,389,187 B1  5/2002  Greenaway et al.
7,772,541 B2  8/2010  Froggatt et al.
(Continued)

OTHER PUBLICATIONS

International Preliminary Report on Patentability for Application No. PCT/US2021/043317 mailed Feb. 23, 2023, 9 pages.
(Continued)

*Primary Examiner* — Dixomara Vargas
(74) *Attorney, Agent, or Firm* — Haynes & Boone, LLP.

(57) ABSTRACT

Systems, devices, methods, and computer program products for identifying and mitigating image-to-body divergence are disclosed herein. In some embodiments, a method includes receiving sensor data from a medical device while the medical device is inserted within an anatomic region of a patient and after it has been registered to an anatomic model of the anatomic region, where the anatomic model is based on previously-obtained image data of the anatomic region and includes a virtual path extending throughout the anatomic model to an anatomic structure of interest, and where sensor data indicates a location of at least a portion of the medical device; comparing the sensor data to a corresponding portion of the virtual path; based at least in part on the comparison, producing a divergence classifier indicative of a divergence of the anatomic region from the anatomic
(Continued)

model; and generating an alert when the divergence classifier exceeds a predetermined threshold.

20 Claims, 8 Drawing Sheets

(51) Int. Cl.
 *A61B 34/20* (2016.01)
 *A61B 34/30* (2016.01)
(52) U.S. Cl.
 CPC ... *A61B 2034/105* (2016.02); *A61B 2034/107* (2016.02); *A61B 2034/2051* (2016.02); *A61B 2034/2061* (2016.02); *A61B 2034/301* (2016.02); *A61B 2034/303* (2016.02)
(58) Field of Classification Search
 CPC ...... A61B 2034/2061; A61B 2034/301; A61B 2034/303
 See application file for complete search history.

(56) References Cited

U.S. PATENT DOCUMENTS

| | | | |
|---|---|---|---|
| 7,781,724 B2 | 8/2010 | Childers et al. | |
| 7,901,348 B2* | 3/2011 | Soper | A61B 1/000096 600/117 |
| 10,706,543 B2 | 7/2020 | Donhowe et al. | |
| 11,202,680 B2 | 12/2021 | Donhowe et al. | |
| 2006/0013523 A1 | 1/2006 | Childers et al. | |
| 2006/0281971 A1* | 12/2006 | Sauer | A61B 34/20 600/101 |
| 2013/0204124 A1* | 8/2013 | Duindam | A61B 17/3468 604/272 |
| 2014/0243660 A1 | 8/2014 | Klinder et al. | |
| 2018/0153621 A1 | 6/2018 | Duindam et al. | |
| 2018/0235716 A1 | 8/2018 | Hane et al. | |
| 2019/0183587 A1 | 6/2019 | Rafii-Tari et al. | |
| 2020/0129045 A1* | 4/2020 | Prisco | A61B 1/0005 |
| 2020/0246079 A1 | 8/2020 | Shevlev et al. | |
| 2020/0275824 A1* | 9/2020 | Tata | A61B 1/0052 |
| 2021/0059766 A1* | 3/2021 | Graetzel | A61G 13/0081 |
| 2021/0128250 A1* | 5/2021 | Chav | A61B 17/56 |
| 2021/0137350 A1* | 5/2021 | Inglis | A61B 1/00016 |
| 2022/0354380 A1* | 11/2022 | Tata | G06T 7/33 |
| 2023/0143522 A1* | 5/2023 | Keast | A61B 34/20 606/130 |
| 2023/0162355 A1* | 5/2023 | Tegzes | G06T 7/10 382/128 |

OTHER PUBLICATIONS

International Search Report and Written Opinion for Application No. PCT/US2021/043317, mailed on Nov. 5, 2021, 15 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

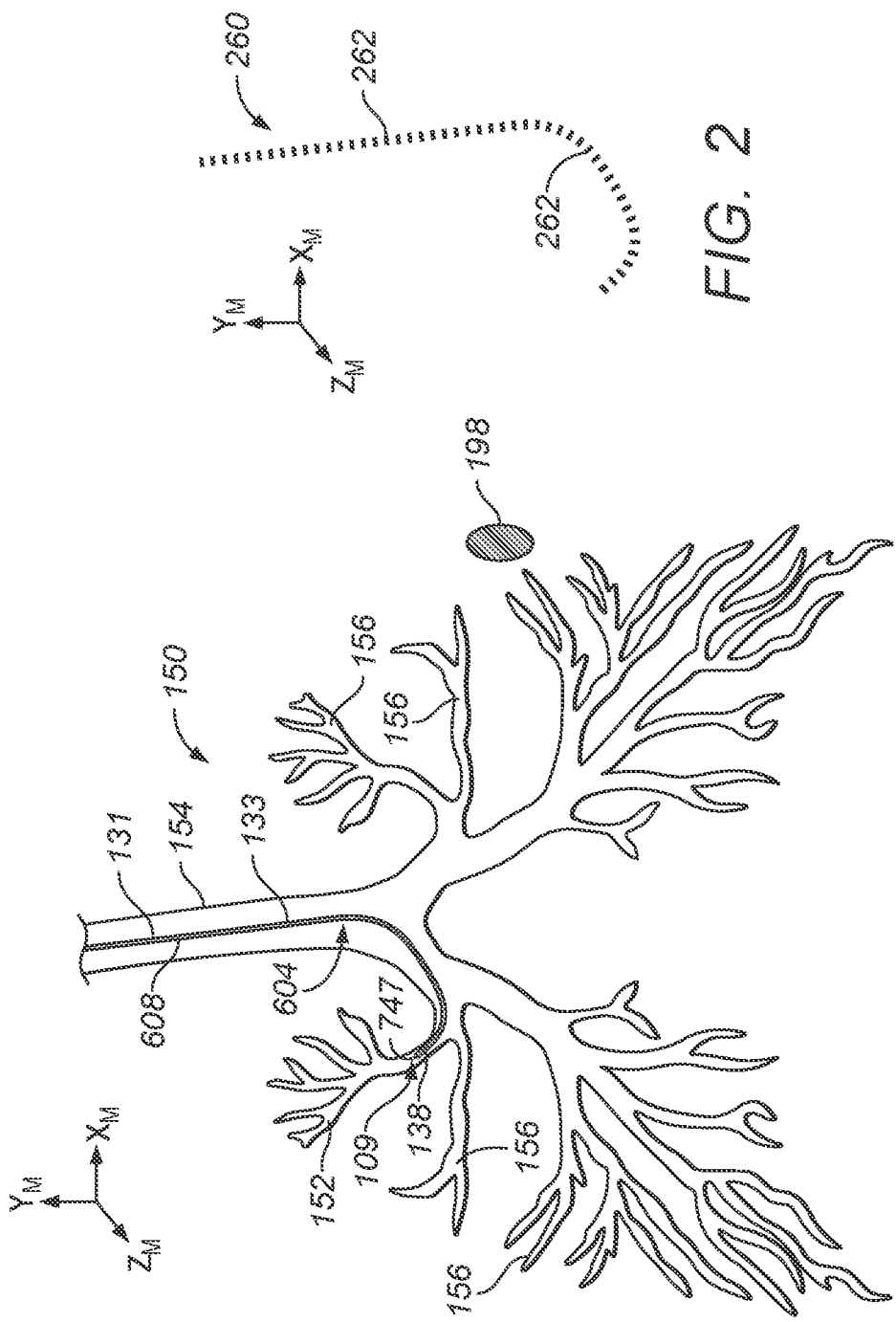

ALERTING AND MITIGATING DIVERGENCE OF ANATOMICAL FEATURE LOCATIONS FROM PRIOR IMAGES TO REAL-TIME INTERROGATION

CROSS-REFERENCE TO RELATED APPLICATION(S)

This patent application is the U.S. National Stage patent application of International Patent Application No. PCT/US2021/043317 filed on Jul. 27, 2021 which claims priority to and the benefit of U.S. Provisional Patent Application No. 63/065,420, filed Aug. 13, 2020, each of which is incorporated herein by reference in its entirety.

TECHNICAL FIELD

The present disclosure is directed to systems, devices, methods, and computer program products for determining, alerting, predicting and/or mitigating divergence of an anatomical feature between a past pre-operative image and a present physical location, particularly during a minimally invasive medical procedure using a medical instrument.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy.

To assist with reaching the target tissue location, the location and movement of the minimally invasive medical tools may be mapped with image data of the patient anatomy, typically obtained prior to medical procedure. The image data may be used to assist navigation of the medical tools through natural or surgically-created passageways in anatomic systems such as the lungs, the colon, the intestines, the kidneys, the heart, the circulatory system, or the like. Yet, several challenges arise in reliably and accurately mapping the medical tools and images of the anatomic passageways, particularly for locating anatomic structures of interest identifiable in the previously-obtained image data.

SUMMARY

Disclosed herein are systems, devices, methods, and computer program products for identifying and mitigating divergence of anatomic structures between prior pre-operative images (e.g., previously obtained images obtained using one or more medical imaging modalities, such as computed tomography (CT) scan images) of a patient's anatomy to sensor data, such as position, location, or shape sensor data obtained from one or more sensors in a medical device while inside the patient's anatomy and/or intraoperative images obtained in real-time by a medical device. Also disclosed are systems, devices, methods, and computer program products for determining the divergence of anatomic structures from an anatomic model and predicting where their actual locations are while the medical device is interrogating the patient's anatomy in real-time.

In some embodiments, for example, a system for determining divergence of an anatomic region from an anatomic model of the anatomic region includes a medical device comprising a sensor, wherein the medical device is insertable within a patient's anatomy; and a computing device in communication with the medical device, where the computing device comprises a processor and a memory, the memory coupled to the processor and storing instructions that, when executed by the processor, cause the system to perform operations comprising: receiving data acquired by the sensor of the medical device while the medical device is inserted within an anatomic region of the patient and after the medical device has been registered to an anatomic model of the anatomic region, wherein the anatomic model is based on previously-obtained image data of the anatomic region and includes a virtual path extending throughout the anatomic model to an anatomic structure of interest, and wherein sensor data indicates a location of at least a portion of the medical device, comparing the sensor data to a corresponding portion of the virtual path, based at least in part on the comparison, producing a divergence classifier indicative of a divergence of the anatomic region from the anatomic model, and generating an alert when the divergence classifier exceeds a predetermined threshold.

In some embodiments, for example, a non-transitory, computer-readable medium can store instructions thereon that, when executed by one or more processors of a computing system, cause the computing system to perform operations comprising: receiving data acquired by a sensor of a medical device while the medical device is inserted within an anatomic region of the patient and after the medical device has been registered to an anatomic model of the anatomic region, wherein the anatomic model is based on previously-obtained image data of the anatomic region and includes a virtual path extending throughout the anatomic model to an anatomic structure of interest, and wherein sensor data indicates a location of at least a portion of the medical device, comparing the sensor data to a corresponding portion of the virtual path, based at least in part on the comparison, producing a divergence classifier indicative of a divergence of the anatomic region from the anatomic model, and generating an alert when the divergence classifier exceeds a predetermined threshold.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

FIG. 1 is a schematic representation of a portion of a medical instrument system inserted within an anatomic passageway of a patient.

FIG. 2 is a diagram illustrating a plurality of coordinate points forming a point cloud representing a shape of the portion of the medical instrument system of FIG. 1 configured in accordance with various embodiments of the present technology.

DETAILED DESCRIPTION

Figure 3:
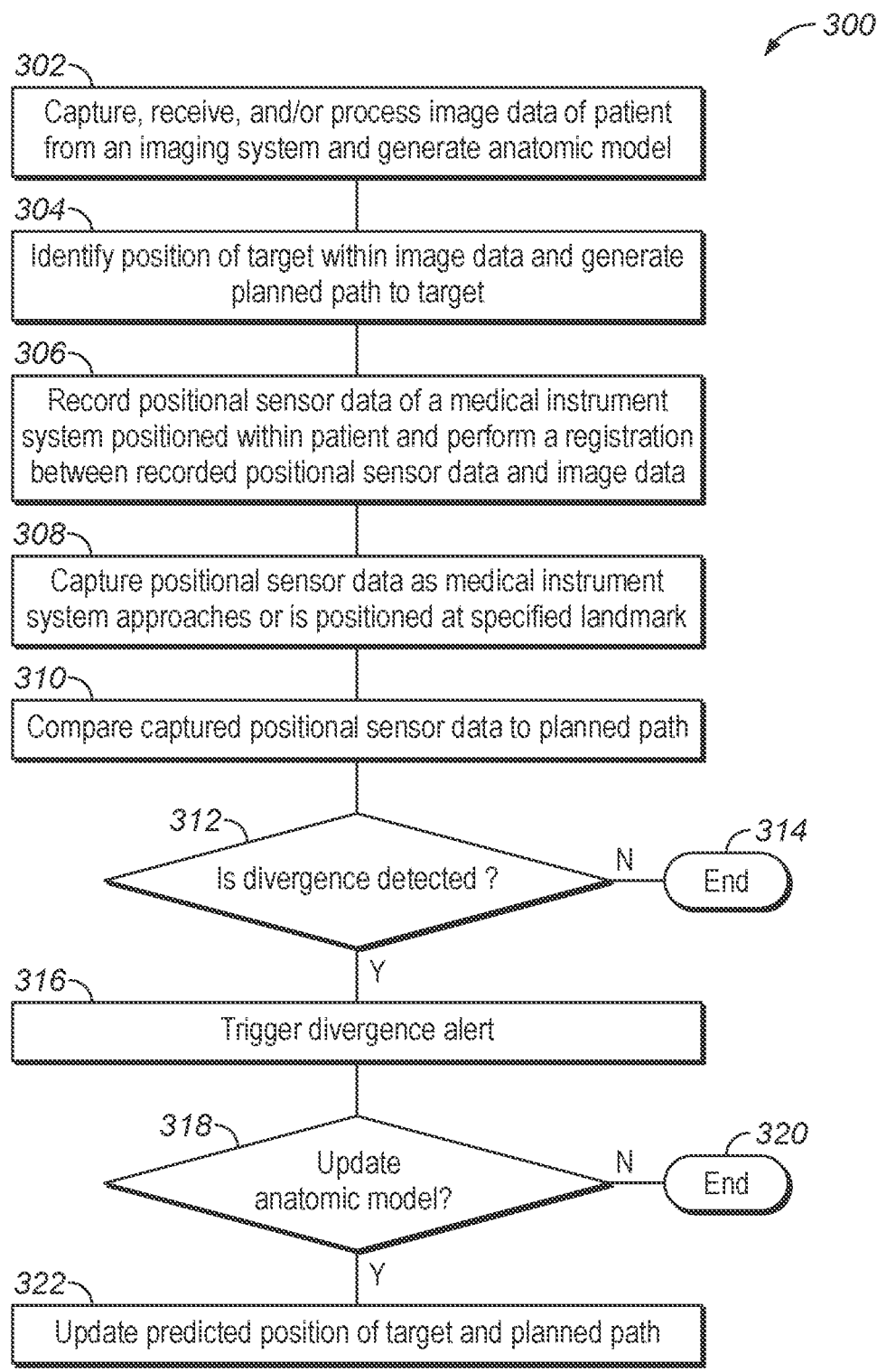
FIG. 3 is a flow diagram illustrating a method for identifying and/or mitigating divergence of a target anatomic structure from a predetermined location along a planned path of the medical instrument system of FIG. 1 in accordance with various embodiments of the present technology.

The present disclosure is directed to systems, devices, methods, and computer program products for identifying and mitigating divergence between (i) an anatomic model generated from prior pre-operative imaging (e.g., obtained using one or more medical imaging modalities, such as CT scan imaging) of patient anatomy and (ii) sensor data, such as position, location, and shape sensor data and/or images obtained in real-time by a medical device positioned within the patient anatomy. Also disclosed are systems, devices, methods, and computer program products for determining the divergence of anatomic structures and predicting where their actual locations are while the medical device is interrogating the patient's anatomy in real-time.

In some implementations, as illustrated by example embodiments below, the disclosed systems, devices, methods and computer program products can be used to determine how target regions of pulmonary airways change from a pre-operative 3D map of the airways constructed before a medical procedure (from image data collected by an imaging system, e.g., CT system) to their actual locations and conformations during the medical procedure while the medical device, such as a robotic catheter, is navigating in the airways based on the 3D map.

While the disclosed embodiments are described herein primarily based on identifying and mitigating divergence of target anatomic structures in the pulmonary airways for the purpose of facilitating understanding of the underlying concepts, it is understood that the disclosed embodiments can also include identifying and mitigating divergence of target anatomic structures in other tissues, organs and organ systems, including but not limited to the colon, the intestines, the kidneys, the heart, the urinary tract, and the circulatory system. Similarly, while the disclosed embodiments pertain to CT-to-body divergence, it is understood other imaging modalities are applicable to the disclosed techniques, including but not limited to magnetic resonance imaging (MRI), X-Ray imaging, ultrasound imaging, and others.

Divergence is a phenomenon where a current location of an anatomic structure within a patient has changed in relation to a previous location of the anatomic structure within the patient that was observed within previously-obtained (or pre-operative) images of the anatomic structure. This phenomenon is referred to herein as "image-to-body divergence," and in the case of specific imaging modalities like CT imaging, it can be referred to as "CT-to-body divergence." In common clinical practice, image-to-body divergence typically occurs when medical images are taken well before a medical procedure, such as weeks or months before the procedure. Image-to-body divergence may also occur shortly before a medical procedure for certain anatomic structures, such as the lungs. For patients who are to undergo a medical procedure directed to interrogating target anatomic structures (e.g., potential tumor sites) identified within previously-obtained medical images (e.g., CT images, MRI images, etc.), image-to-body divergence of the target anatomic structure is a relatively common occurrence by the time the patient undergoes the medical procedure. This can complicate or even thwart the medical procedure, as target sites may be difficult or impossible to locate by the physician performing the procedure using currently-available medical device(s). For example, image-to-body divergence of a patient's lungs may occur on the same day as the pre-operative imaging, e.g., because of differences in the patient's manner of breathing during pre-operative imaging (controlled breathing via mechanical ventilation) and during the medical procedure (natural breathing), as well as due to effects of lung contraction and atelectasis—any of which can create and exacerbate image-to-body divergence, which in turn can greatly influence the medical procedure.

Image-to-body divergence can be a result of both inherent and external causes. For example, pulmonary structures naturally change shape in a medical procedure for a variety of reasons (referred to as "natural deformation"). These reasons include atelectasis, discrepancies between the patient's body position and manner of breathing (e.g., breath hold, positive pressure ventilation versus spontaneous breathing) during the prior pre-operative imaging and during the medical procedure, and/or changes in pulmonary anatomy itself, such as a change in the target tumor or lung since the prior imaging (especially when the imaging was performed several weeks to months prior to the medical procedure). Also, pulmonary structures can change shape due to "induced deformation." Induced deformation can be caused by a medical device pushing on airway walls while performing the procedure and/or by an intubation angle that can change the tilt of airways in the patient's body.

For a pulmonary diagnostic procedure (e.g., for a biopsy of tissue in or around airways of the lungs), pre-operative images of pulmonary structures can be overlaid to create a 3D map or model of the pulmonary structures that can be used to inform a medical device user (e.g., a physician) where and how to navigate the medical device through the pulmonary structures to reach a target anatomic structure or region. Because the 3D map or model is based on pre-operative images, image-to-body divergence may cause the physician to drive the medical device to a correct location within the 3D map or model where the system had mapped the target anatomic structure but at which the target anatomic structure is no longer positioned, resulting in missed diagnosis or improper intervention because the target anatomic structure was not found or reached and/or an incorrect tissue sample was acted upon. Conventional techniques to create a 3D map and navigation plan have not addressed or have been unable to accurately account for image-to-body divergence. Moreover, existing techniques to create a 3D map and navigation plan for a medical instrument do not provide the medical device user with adequate and timely notice of image-to-body divergence of the target structure being navigated towards.

The present technology provides techniques for identifying and determining the extent of image-to-body divergence, and for mitigating such image-to-body divergence by generating alerts and/or predicting a true location of target anatomical structures determined to have diverged from previously-obtained images, e.g., pre-operative images. For example, the disclosed techniques generate an anatomic model of an anatomic region based on pre-operative images of the anatomic region. Based on the pre-operative images, the disclosed techniques also generate a planned path for a user to navigate a medical device throughout the anatomic region to arrive at a target anatomic structure identified within the pre-operative images. The planned path is projected onto the anatomic model. Once the medical device is positioned within the anatomic region and the medical device is registered to the anatomic model, a user can use the anatomic model and the planned path to navigate the medical device toward the target anatomic structure within the anatomic region. At various points during the navigation (e.g., as the medical device passes anatomic landmarks, as the medical device navigates a specified distance, as the medical device approaches the end of the planned path, as the medical device approaches the target anatomic structure, etc.), the disclosed techniques can compare (i) one or more planned locations of one or more portions (e.g., a planned location of the tip) of the medical device along the planned path to (ii) one or more current locations of the corresponding portion(s) (e.g., a current location of the tip) of the medical device extracted from position sensor data (e.g., shape data) captured by one or more sensors of the medical device. The difference(s) between the current location(s) and the corresponding planned location(s) can provide indications of the magnitude and direction of divergence between the anatomic region and the anatomic model. In some implementations of the disclosed techniques, the user is alerted when the determined divergence is above a predetermined threshold, e.g., such as a predetermined distance of divergence. Furthermore, because motion of the target anatomic structure is correlated with motion of the anatomic region local to the target anatomic structure, in some implementations, the disclosed techniques can (i) evaluate the difference(s) between the current location(s) and the planned location(s) as the medical device approaches the planned position of the target anatomic structure to predict the target anatomic structure's current position and (ii) update the anatomic model to reflect the predicted position. Thus, the present technology mitigates the effects of CT-to-body divergence on the anatomic model in a manner agnostic to the source or reason for the divergence and facilitates navigation of the medical device to a likely current position of the target anatomic structure, thereby increasing the likelihood of a successful medical procedure.

These and other embodiments are discussed in greater detail by the examples below.

A. EMBODIMENTS OF TECHNIQUES FOR IDENTIFYING AND MITIGATING IMAGE-TO-BODY DIVERGENCE

FIG. 1 is a schematic representation of a portion of a medical instrument system 604 configured in accordance with various embodiments of the present technology, which is inserted within an anatomic region 150 (e.g., human lungs) of a patient, such as during a medical procedure. As shown in the diagram of FIG. 1, the portion of the medical instrument system 604 inserted into the anatomical region includes an elongate device 131, which is extended within branched anatomic passageways 152 of the anatomic region 150. In this example, the anatomic passageways 152 include a trachea 154 and a plurality of bronchial tubes 156 of the lungs.

In some embodiments, the elongate device 131 is part of a flexible catheter or other biomedical device that can be sized and shaped to receive a medical instrument and to facilitate delivery of the medical instrument to a distal portion 138 of the elongate device 131 for various purposes. For example, the medical instrument of the medical instrument system 604 can be used for medical procedures, such as for survey of anatomic passageways, surgery, biopsy, ablation, illumination, irrigation, and/or suction. The medical instrument can include positional sensors, rate sensors, image capture probes, biopsy instruments, laser ablation fibers, and/or other surgical, diagnostic, and/or therapeutic tools. Further details regarding the medical instrument system 604 are described in greater detail below in connection with FIGS. 6 and 7.

In some example embodiments (discussed in greater detail below in connection with FIG. 7), the elongated device 131 can include an endoscope or other biomedical devices having one or more image capture devices 747 positioned at the distal portion 138 of the elongated device 131 (as in the example shown in FIG. 1) and/or at other locations along the elongated device 131. In these embodiments, the one or more image capture devices 747 can capture one or more real navigational images or video (e.g., a sequence of one or more real navigational image frames) of anatomic passageways and/or other real patient anatomy while the elongated device 131 is within the anatomic region 150 of the patient.

In the example implementation shown in FIG. 1, the elongate device 131 has a position, orientation, pose, and shape within the anatomic region 150, all or a portion of which (in addition to or in lieu of movement, such as speed or velocity) can be captured as positional sensor data. In this or other examples, a positional sensor system 608 in communication with the medical instrument system 604 is configured to acquire the position sensor data from at least one sensor of the elongate device 131. In various embodiments of the medical instrument system 604, for example, at least one sensor of the elongate device 131 can include a shape sensor 133 and/or one or more position measuring devices (each discussed later in greater detail below in connection with FIG. 7). In some implementations, the positional sensor system 608 can survey the anatomic passageways 152 by gathering positional sensor data of the medical instrument system 604 within the anatomic region 150 in a frame of reference of the medical instrument and/or elongated device 131, e.g., a cartesian coordinate system frame of reference (XM, YM, ZM). The positional sensor data may at least in part be recorded as a set of two-dimensional or three-dimensional coordinate points.

In the example of the anatomic region 150 being human lungs, the coordinate points may represent the locations of the distal portion 138 of the elongate device 131 and/or of other portions of the elongate device 131 while the elongate device 131 is advanced through the trachea 154 and the bronchial tubes 156. In these and other embodiments, the collection of coordinate points may represent the shape(s) of the elongate device 131 while the elongate device 131 is advanced through the anatomic region 150. Still, in these and other embodiments, the coordinate points may represent positional data of other portions of the medical instrument system 604.

The set of 2D and/or 3D coordinate points from the recorded positional sensor data may together be used to form a point cloud. For example, FIG. 2 is a diagram illustrating a plurality of coordinate points 262 forming a point cloud 260 representing a shape of the portion of the elongate device 131 of FIG. 1 configured in accordance with various embodiments of the present technology. In various implementations, for example, the point cloud 260 is generated from the union of all or a subset of the coordinate points 262 recorded by the positional sensor system 608, e.g., while the elongate device 131 is in a stationary position.

In some embodiments, a point cloud (e.g., the point cloud 260) can include the union of all or a subset of coordinate points recorded by the positional sensor system 608 during a data capture period that spans multiple shapes, positions, orientations, and/or poses of the elongate device 131 within the anatomic region 150. In these embodiments, the point cloud can include coordinate points captured by the positional sensor system 608 that represent multiple shapes of the elongate device 131 while the elongate device 131 is advanced or moved through patient anatomy during the image capture period. Additionally, or alternatively, because the configuration, including shape and location, of the elongate device 131 within the patient may change during the image capture period due to anatomical motion, the point cloud in some embodiments can comprise the plurality of coordinate points 262 captured by the positional sensor system 608 that represent the shapes of the elongate device 131 as the elongate device 131 passively moves within the patient.

A point cloud of coordinate points captured by the positional sensor system 608 can be registered to different models or datasets of patient anatomy. For example, a point cloud of coordinate points can be registered to previously-obtained (pre-operative) image data of the anatomic region 150 captured by an imaging system. In some implementations, for example, the previously-obtained image data of the anatomic region 150 is used to generate an anatomic model of the anatomic region. The elongate device 131 can be registered to the anatomic model based on the positional sensor data generated by the positional sensor system 608 (and/or to endoscopic image data generated by the one or more image capture devices 747, if applicable) to (i) map the tracked position, orientation, pose, shape, and/or movement of the medical instrument system 604 within the anatomic region 150 to a correct position in real-time within the anatomic model, and/or (ii) determine a virtual navigational image of virtual patient anatomy of the anatomic region 150 from a viewpoint of the medical instrument system 604 at a location within the anatomic model 150 corresponding to a location of the elongate device 131 within the patient.

Referring back to FIG. 1, the anatomic region 150 includes an anatomic structure of interest 198 (also referred to as a "target anatomic structure" or "target"), e.g., such as suspected tumorous tissue. In some implementations, the target 198 is mapped to the anatomic model of the anatomic region 150 based on the physical location of the target 198 relative to the anatomic region 150 observed in previously-obtained (pre-operative) image data. The anatomic model can further provide a planned path for the user to navigate the elongated device 131 to the target anatomic structure 198 during a medical procedure. After the medical instrument system 604 is registered to the anatomic model, the planned path can be updated based on the tracked position, orientation, pose, shape, and/or movement of the elongate device 131 within the anatomic region 150. The planned path can be manifested on virtual navigational image(s) of virtual patient anatomy of the anatomic region 150 from the viewpoint of the medical instrument system 604, which can be represented as a line or series of points along one or more views of the anatomic region 150 of the generated anatomic model corresponding to a location of the medical instrument system 604 within the patient. Examples of virtual navigational image(s) associated with the anatomic model depicting a portion of an example planned path to the target 198 are discussed in greater detail below in connection with FIGS. 4A-4C and/or FIGS. 5A and 5B.

Yet, as discussed above, due to image-to-body divergence the user cannot be certain that the target 198 is in the same location at the time of the medical procedure as it was at the time the previously-obtained, pre-operative image data was acquired. Thus, the user also cannot be certain that the target 198 is at the location depicted in the anatomic model and in the virtual navigational images. Therefore, the medical instrument system 604 can be implemented to identify and/or mitigate potential image-to-body divergence based on the following techniques in accordance with the present technology.

FIG. 3 is a flow diagram illustrating a method 300 for identifying divergence of an anatomic region from an anatomic model of the anatomic region that was generated from previously-obtained, pre-operative image data of the anatomic region in accordance with various embodiments of the present technology. The flow diagram of FIG. 3 further illustrates how the method 300 can be implemented to mitigate the identified divergence, e.g., such as alerting a user of a medical device and/or predicting an actual position of the target anatomic structure, which can be used for redirecting navigation of a medical device, also in accordance with various embodiments of the present technology.

The method 300 is illustrated as a set of operations or processes 302-312, which can optionally include processes 314-322 in various ways or combinations. All or a subset of the processes of the method 300 can be implemented by a medical instrument operating in conjunction with a computing device, such as a control system in communication with or integrated with a medical system comprising the medical instrument. Alternatively or in combination, all or a subset of the processes of the method 300 can be implemented by a control system of a medical instrument system or device, including but not limited to various components or devices of a robotic or teleoperated system 600, as described in greater detail below in connection with FIGS. 6 and 7, as well as any other suitable system. The computing device or control system for implementing the method 300 can include one or more processors operably coupled to a memory storing instructions that, when executed, cause the computing system to perform operations in accordance with some or all of the processes 302-310 and/or processes 312-322 of the method 300. Additionally, or alternatively, all or a subset of the processes of the method 300 can be executed by an operator (e.g., a physician, a user, etc.) of the system 600. Furthermore, any one or more of the processes of the method 300 can be executed in accordance with the discussion above. Several of the processes 302-322 are discussed below with continual reference to one or more of FIGS. 4A-5B to facilitate clarity and understanding of the present technology.

At process 302, the method 300 captures, receives, and/or processes image data of an anatomic region of the patient from an imaging system and generates an anatomic model. In some implementations, the imaging system is a CT imaging system or another imaging system. In some implementations of the process 302, the image data can be captured, received, and/or processed during an image capture period of the imaging system. The image capture period can correspond to a time period during which the imaging system is activated. In some embodiments, for example, the image capture period can be pre-operative such that the image data is captured, received, and/or processed before (e.g., minutes, hours, days, weeks, months, etc.) the medical procedure in which medical instrument system is advanced into the patient. In other embodiments, the image capture period can be intraoperative such that the image data of the patient is captured, received, and/or processed while the medical instrument system is positioned within the patient. In these embodiments, the medical instrument system may be stationary during the image capture period, may be subject to commanded movement (e.g., operator-commanded advancement or bending) during the image capture period, and/or may be passively moving (e.g., subject to no commanded movement but subject to anatomical motion from respiratory activity, cardiac activity, or other voluntary or involuntary patient motion) during the image capture period. In still other embodiments, the image capture period can be postoperative such that the image data of the patient is captured, received, and/or processed after the medical instrument system is removed from the patient. In some implementations of the process 302, for example, the image data can be captured, received, and/or processed in real-time or near real-time.

Figure 5A:
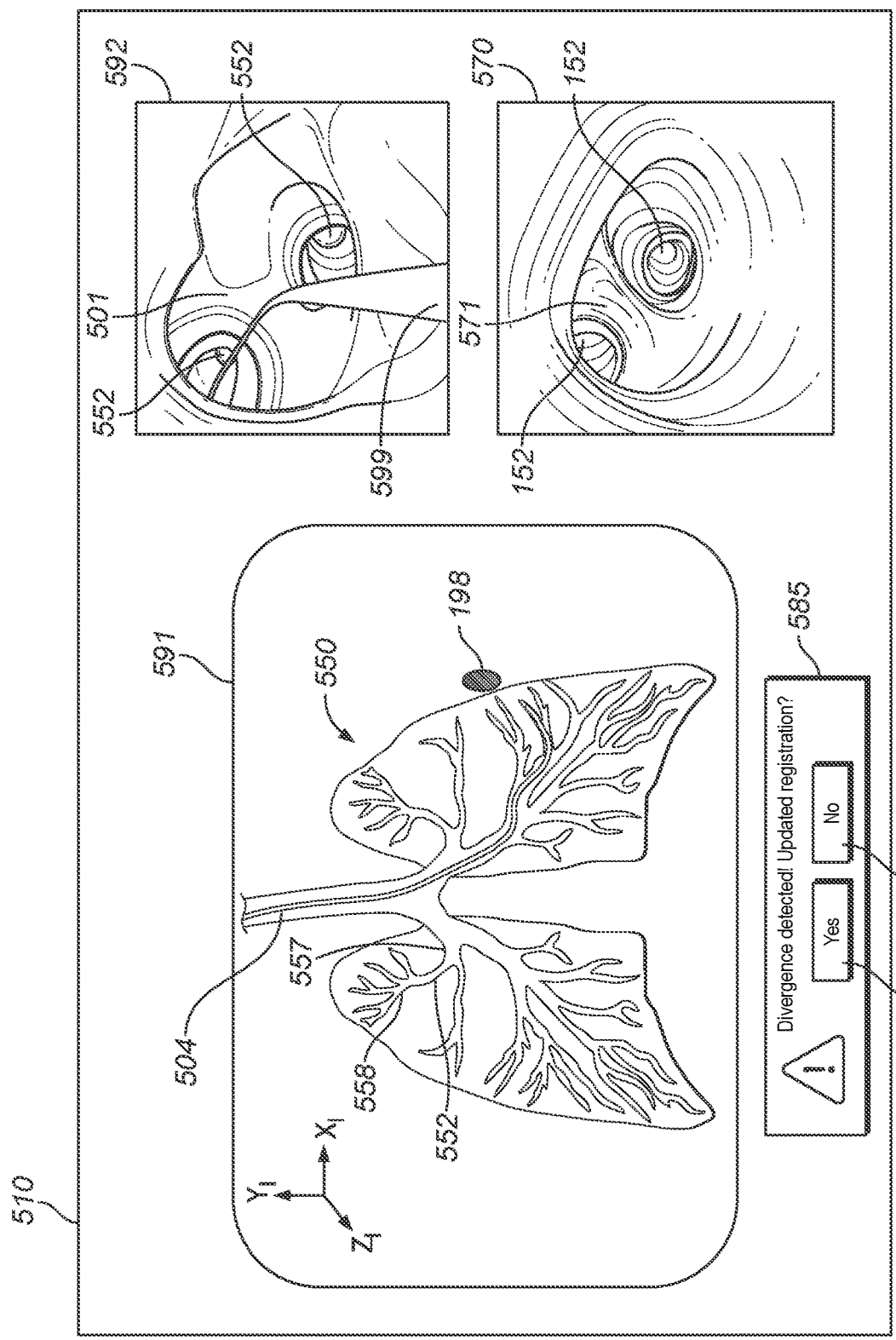
FIGS. 5A and 5B are schematic representations of displays of a display system in accordance with various embodiments of the present technology.
Figure 5B:
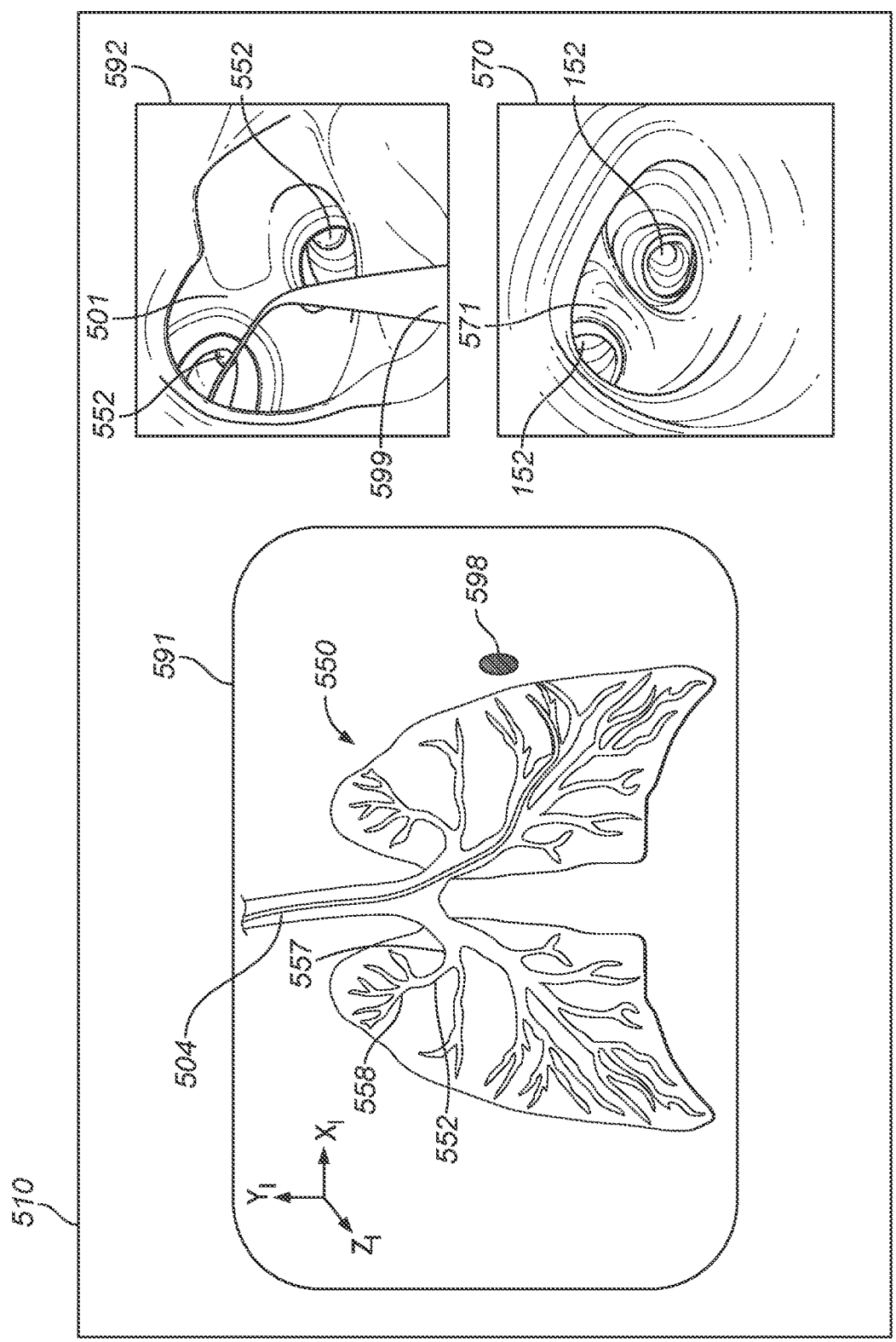

The captured, received, and/or processed image data of the patient can include graphical elements representing anatomical features of the patient and, in the case of intraoperative image data, the captured, received, and/or processed image data can include graphical elements representing the medical instrument system. In some implementations of the process 302, for example, the anatomic model of the anatomical features of the patient can be generated by segmenting and filtering the graphical elements included in the image data. For example, during a segmentation process, pixels or voxels generated from the image data may be partitioned into segments or elements and/or be tagged to indicate that they share certain characteristics or computed properties such as color, density, intensity, and texture. In some embodiments, less than all of the image data may be segmented and filtered. The segments or elements associated with anatomical features of the patient are then converted into an anatomic model, which is generated in an image reference frame (XI, YI, ZI). Examples of the generated anatomic model are depicted in FIGS. 5A and 5B, and are discussed in greater detail below.

At process 304, the method 300 identifies the position of one or more target anatomic structures relative to the anatomic region from the image data and generates a planned path to the target(s) via anatomic passageways of the generated anatomic model. The planned path provides a map for navigating a medical instrument (e.g., an elongated device 131 of the medical instrument system 604 as shown in FIG. 1) throughout the imaged anatomic region, such as via anatomic passageways like pulmonary airways, toward the target(s). In some implementations of the process 304, for example, the planned path can be generated on a virtual navigational image (or set of virtual navigational images) that provide a virtual map of the patient's anatomy. FIG. 4A, discussed in greater detail below, illustrates an example of a planned path 452 overlaid on a virtual image of a portion of the anatomic region 150, e.g., lungs, of the patient.

At process 306, the method 300 records positional sensor data of a medical instrument system (e.g., the medical instrument system 604) positioned within the anatomic region and performs a registration between the recorded positional sensor data and the image data. In some implementations of the process 306, the positional sensor data is recorded using a positional sensor system (e.g., the positional sensor system 608), which can be recorded during a position data capture period of the positional sensor system. For example, the positional sensor data provides positional information (e.g., shape, position, orientation, pose, movement, etc.) of the medical instrument system while at least a portion of the medical instrument system is located within the anatomic region. The position data capture period can correspond to a time period during which a shape sensor and/or one or more other positional sensors of the positional sensor system are activated to collect and record positional sensor data. For example, during the position data capture period, the medical instrument system may be stationary, may be subject to commanded movement (e.g., operator-commanded advancement or bending), and/or may be passively moving (e.g., subject to no commanded movement but subject to anatomical motion from respiratory activity, cardiac activity, or other voluntary or involuntary patient motion). In some implementations of the process 306, the positional sensor data can be at least partially recorded as one or more coordinate points in two or three dimensions in the medical instrument reference frame (XM, YM, ZM), e.g., which can be related to a surgical reference frame (XS, YS, ZS) in example implementations in a surgical environment. In these and other implementations, for example, a coordinate point corresponding to the positional sensor data can be associated with a timestamp, which can be included as part of the recorded positional sensor data.

In some implementations of the process 306, the registration of the medical instrument system based on the recorded positional sensor data and the image data involves aligning the medical instrument frame of reference (XM, YM, ZM) (and/or the surgical reference frame (XS, YS, ZS)) with the image reference frame (XI, YI, ZI). In some embodiments of the process 306, the registration includes generating a point cloud of the recorded positional sensor data. In various implementations, for example, the point cloud can be generated from the union of all or a subset of the coordinate points associated with the recorded positional sensor data, e.g., during one or more position data capture periods of the positional sensor system. For example, the point cloud can represent one or more shapes of the medical instrument system as the medical instrument system is stationary and/or is actively or passively moved within the patient. In these and other implementations, the point can represent the location of one or more portions (e.g., a tip) of the medical instrument system over time (e.g., over multiple data capture periods). In various examples, the point cloud may be generated in two or three dimensions in the medical instrument reference frame (XM, YM, ZM).

The medical instrument reference frame (XM, YM, ZM) can be registered to the anatomic model in the image reference frame (XI, YI, ZI). This registration may rotate, translate, or otherwise manipulate by rigid and/or non-rigid transforms coordinate points of the point cloud to align the coordinate points with the anatomic model. The transforms may be six degrees-of-freedom transforms, such that the point clouds may be translated or rotated in any or all of X, Y, Z, pitch, roll, and yaw. In some implementations of the registration between recorded positional sensor data and the image data at the process 306, the method 300 uses an iterative closest point (ICP) algorithm to perform the registration. For example, the method 300 can (i) compute a point-to-point correspondence between coordinate points in the point cloud to points (e.g., on a centerline or at other locations) within the anatomic model and (ii) compute an optimal transform to minimize Euclidean distances between corresponding points. The registration between the recorded positional sensor data in the instrument frame of reference and the image data in the image reference frame may be achieved, for example, by using a point-based ICP technique, as described in U.S. Provisional Pat. App. Nos. 62/205,440 and 62/205,433, which are both incorporated by reference herein in their entireties. In other implementations of the process 306, the registration can be performed using another technique.

At process 308, the method 300 captures positional sensor data at various times as the medical instrument system (e.g., the elongated device 131 of the medical instrument system 604) is navigated (e.g., driven) along the planned path generated at the process 304 en route to the target(s). In some implementations, these various times correspond to times the medical instrument system is positioned at anatomic landmarks, has navigated a specified distance, is approaching the end of the planned path, is approaching the target(s), and/or to other specified events. For example, in various implementations of the process 308, the medical instrument system is navigated along the planned path generated at the process 304 en route to a target when it is determined that the medical instrument system is proximate a recognizable anatomical landmark. In some examples pertaining to the anatomic region being anatomic passageways, the specified landmark may include a branch division point in the anatomic passageways. In examples where the anatomic passageways are pulmonary airways of the lungs, as in the anatomic region 150 of FIG. 1, the specified landmark may include a carina. For example, in such implementations, the process 308 can include a verification technique where the operator of the medical instrument system checks to ensure the medical instrument system is being driven along the correct pathway in accordance with the planned path (en route to the target(s)). In some embodiments, the verification technique can include instructing the operator to drive the medical instrument system to nearest landmarks along the navigated path, such as carinas in the driven path, and obtain image(s) using the one or more image capture devices 747 to compare with expected carinas along the planned path based on the virtual navigational image(s) associated with the virtual map of the patient's anatomy.

Figure 4B:
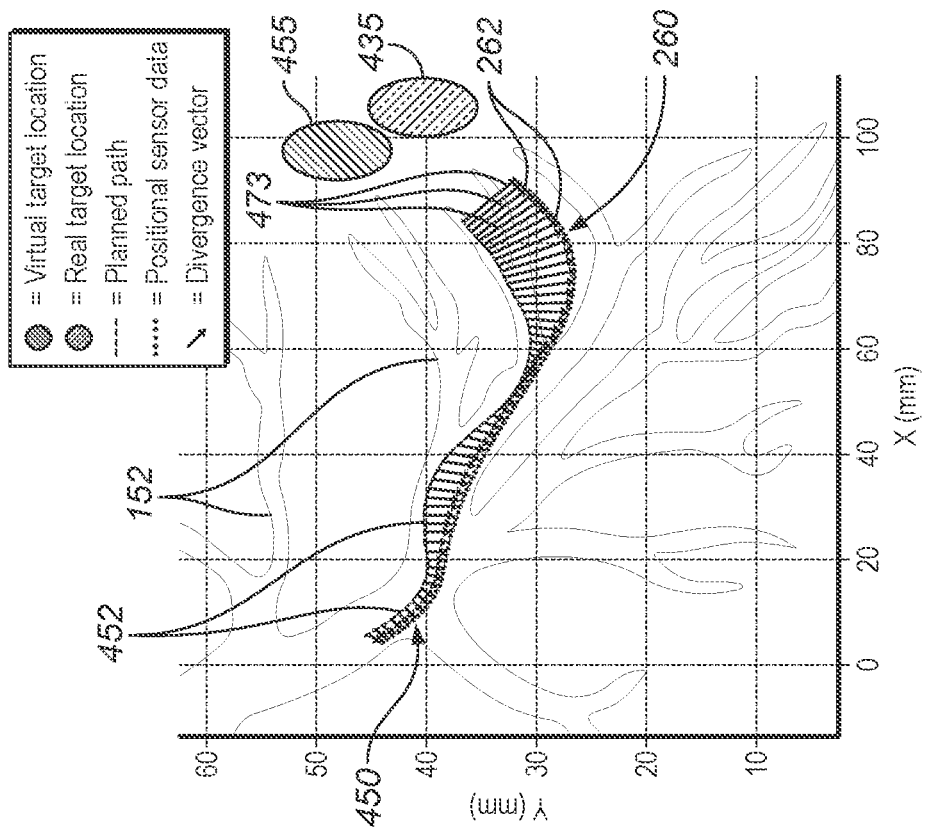
FIGS. 4A-4C are diagrams showing virtual navigation images for a medical instrument system using an anatomic model that depicts divergence of a target anatomic structure in accordance with various embodiments of the present technology.
Figure 4A:
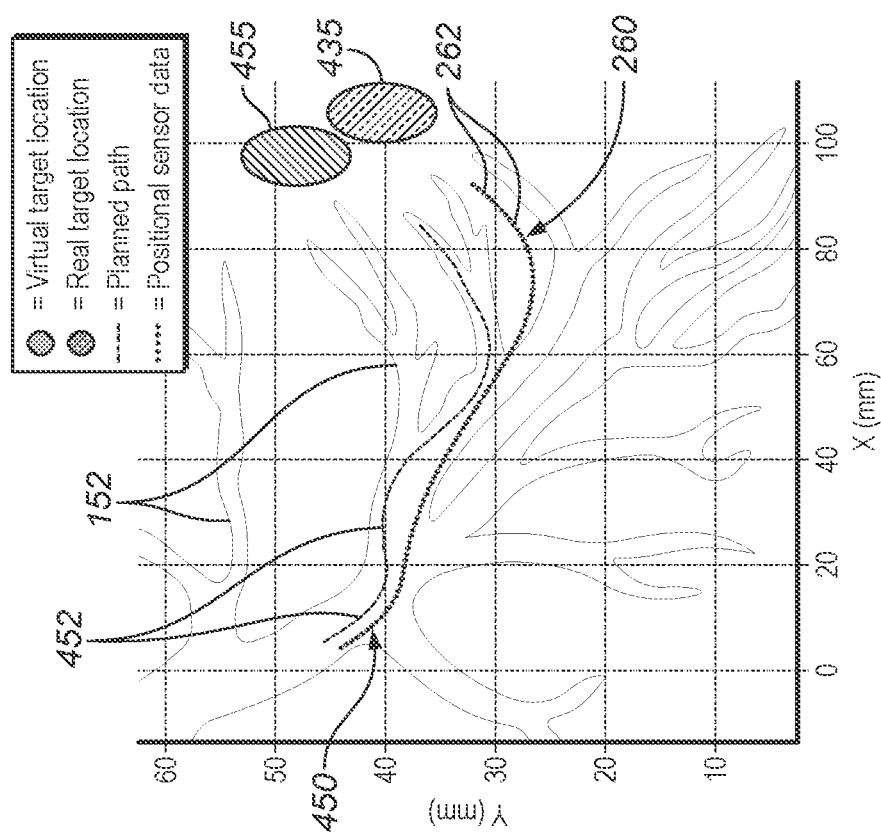
Figure 4C:
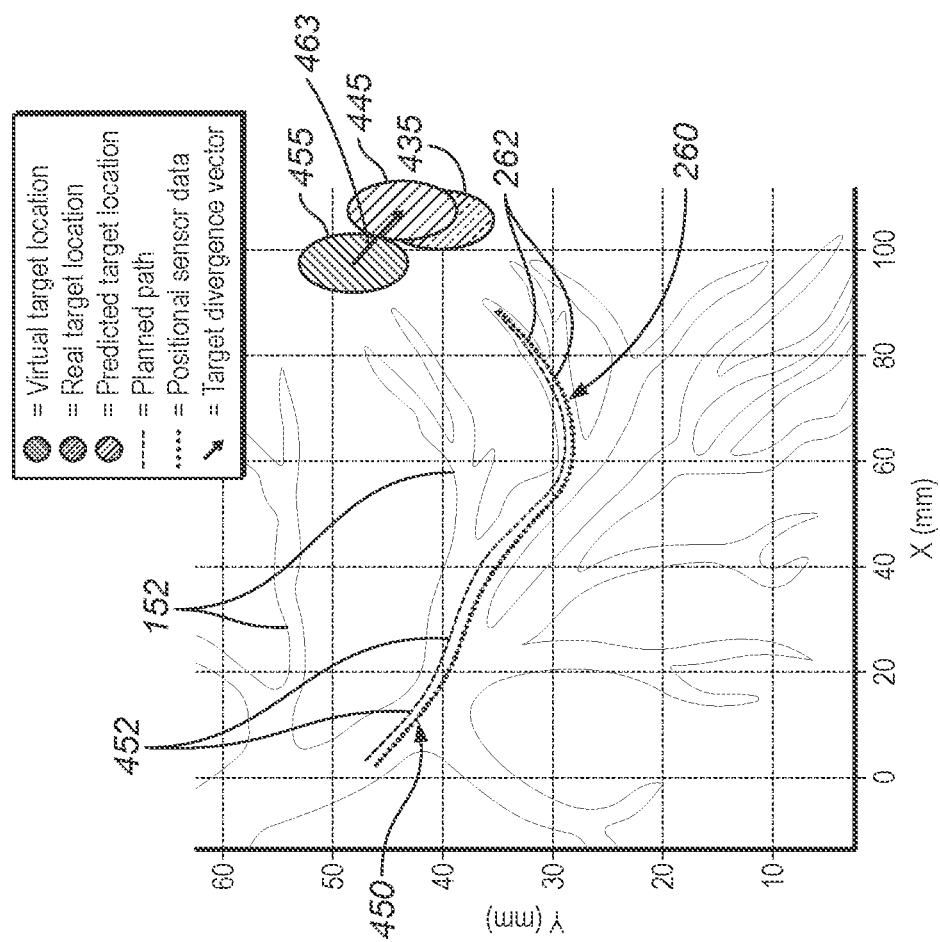

FIGS. 4A-4C are provided to help further illustrate certain aspects of the method 300 of FIG. 3. FIG. 4A, for example, is a partially schematic diagram showing an example of a virtual navigation image for a medical instrument system based on an anatomic model 450 (e.g., generated at the process 302 and/or the process 304 of the method 300) of the anatomic region. The virtual navigation image includes a planned path 452 that navigates anatomic passageways 152 of the anatomic model 450 towards a virtual target location 455. The virtual target location 455 is positioned at a location relative to the anatomic model 450 at a location that corresponds to a location of a target anatomic structure 198 relative the anatomic region that was previously determined from pre-operative image data of the anatomic region. Also shown in FIG. 4A is point cloud 260 composed of the plurality of positional coordinate points 262 that are associated with a current or recent position (e.g., shape) of the medical instrument system within the anatomic region. One of more of the coordinate points 262 can be captured as the medical instrument system is navigated through the anatomic region in accordance with the planned path 452. For example, the coordinate points 262 of the point cloud 260 can be captured as the medical instrument system approaches or reaches the end of the planned path 452.

Continuing with the above example, although the medical instrument system has been navigated to a location within the anatomic region that corresponds to the end of the planned path 452 within the anatomic model 450, the position of the point cloud 260 in the image frame of reference diverges from the position of the planned path 452 in the image frame of reference. That is, the anatomic region has diverged from the anatomic model 450 at least along the portion of the anatomic region that corresponds to the illustrated point cloud 260. Also, because the position of the target 198 (FIG. 1) moves in correlation with the anatomic region local to the target, the real position of the target (represented by real target location 435 in FIG. 4A) has also diverged from the virtual target location 455. Thus, should a user attempt to navigate to the virtual target location 455 from the current location of the medical instrument system shown by the point cloud 260, the medical instrument system is unlikely to encounter the target that is now positioned at a location corresponding to the real target location 435 shown in the virtual image. As such, the chances of a successful medical procedure (e.g., biopsy of the target 198 (FIG. 1), ablation of the target 198, etc.) in this scenario are significantly reduced.

That said, the difference between the planned path 452 and the point cloud 260 can provide an indication of the direction and magnitude of the divergence between the anatomic region and the anatomic model. Therefore, referring to FIGS. 3 and 4A together, the method 300 at process 310 compares the captured positional sensor data (e.g., all or a subset of the coordinate points 262 of point cloud 260) to the planned path 452. In implementations of the process 310, the comparison between the positional sensor data and the planned path can match positional sensor data to one or more points along the planned path 452. For example, the comparison can match one or more points along the planned path that correspond to specified landmarks (e.g., carina(s)) to positional sensor data (e.g., one or more coordinate points 262) of the medical instrument system nearest to the specified landmarks. In some examples, the positional sensor data (e.g., the one or more coordinate points 262) of the medical instrument system used in the comparison with the specified landmarks correspond to position(s) of the distal portion 138 of the elongate device 131 (FIG. 1). Additionally or alternatively, the comparison between the positional sensor data and the planned path 452 can match an end point of the planned path 452 to positional sensor data (e.g., a coordinate point 262) corresponding to the location of the distal portion 138 (e.g., a distal end or another portion) of the medical instrument system. In this manner, the process 310 can be implemented using implementations of the medical instrument system that may only include a single sensor—such as a positional sensor or rate sensor located at a known location relative to the dimensions of the medical instrument system—as well as using embodiments of the medical instrument system that include multiple sensors and/or shape sensors. For example, the process 310 can be implemented using one or more positions determined by a single sensor such as an electromagnetic (EM) sensor, e.g., preferably at the distal portion 138 of the elongate device 131, to determine an offset with the planned path using a divergence vector from that position of the elongate device. Yet, in another example, the process 310 can be implemented using one or more positional data points along the body of the elongate device 131 acquired by the shape sensor 133, which can be correlated to the shape of the airway by comparing to a greater portion of the planned path. Additionally or alternatively, for example, the comparison between the positional sensor data and the planned path 452 can include sampling a subset of the positional sensor data and/or of the points along the planned path 452 such that a first number of positional sensor data points are matched to the same number of points along the planned path 452.

In some implementations, the comparison of the planned path 452 to the positional sensor data (e.g., to coordinate points 262 of the point cloud 260) can include determining an offset from the planned path to the position of the medical instrument system indicated by the positional sensor data. In one embodiment, for example, the offset can be determined using vectors (referred to hereinafter as "divergence vectors") pointing from one or more points along the planned path to the determined position of one or more portions of the medical instrument system indicated by one or more corresponding positional sensor data points (e.g., coordinate points 262), or vice versa. For example, the divergence vectors can be represented as:

> Divergence Vector $x,y,z$=Positional Sensor Data Point $x,y,z$–Matched Point $x,y,z$ along Planned Path, where there is a Divergence Vector $x,y,z$ for every pair of matched points.

FIG. 4B is a schematic diagram showing the virtual navigation image of FIG. 4A. As shown in FIG. 4B, coordinate points 262 of the point cloud 260 are matched with corresponding points along the planned path 452. For example, coordinate points 262 of the point cloud 260 are matched with the nearest points along the planned path 452. In these and other implementations, the coordinate point 262 at the end of the point cloud 260 is matched with a point at the end of the planned path 452. In these and still other implementations, one or more points along the planned path 452 corresponding to one or more anatomic landmarks within the anatomic model 450 are matched with the nearest coordinate points 262 of the point cloud. As discussed above, should there be more points along the planned path 452 than coordinate points 262 in the point cloud 260 (or vice versa), the points along the planned path 452 or the coordinate points 262 can be down-sampled such that there a number of points along the planned path 452 are matched with the same number of coordinate points 262 in the point cloud 260.

Divergence vectors 473 are shown in FIG. 4B between points along the planned path 452 and corresponding coordinate points 262 in the point cloud 260. Each divergence vector 473 can be calculated using the formula provided above. Furthermore, each divergence vector 473 provides an indication (magnitude and direction) of the divergence of the anatomic region from the anatomic model 450 at a location corresponding to the coordinate points 262 in the point cloud 260.

As discussed in greater detail below, the relevance of a given divergence vector 473 can differ from the relevance of other divergence vectors 473 illustrated in FIG. 4B. For example, divergence vectors 473 corresponding to coordinate points 262 in the point cloud 260 that indicate the position of the distal portion (e.g., a distal end) of the medical instrument system can have a higher relevance than divergence vectors 473 that correspond to coordinate points 262 in the point cloud 260 that indicate the position of more proximal portions of the medical instrument system. This is because anatomic passageways 152 are generally expected to decrease distally in size (e.g., diameter), which is expected to make distal portions of the anatomic passageways 152 more susceptible to CT-to-body divergence. Another reason the relevance of two divergence vectors 473 can differ is that movement of a portion of the anatomic region local to a target (e.g., target 435) is expected to impact the position of the target to a greater extent than movement of another portion of the anatomic region further away from the target. Thus, divergence vectors 473 corresponding to portions of the medical instrument system proximate the target (e.g., target 435) are expected to provide a better indication of the current position of the target than divergence vectors 473 corresponding to portions of the medical instrument system further from the target. Thus, the method 300 can consider all or a subset of the divergence vectors 473 generated by the process 310 of the method 300 (e.g., a set number of divergence vectors 473 nearest the target 198, another anatomic landmark, or the distal region (e.g., the distal end) of the medical instrument system; all divergence vectors within a specified distance of the target (e.g., target 435), another anatomic landmark, or the distal region (e.g., the distal end) of the medical instrument system; etc.), and/or the method 300 can apply different weightings to the divergence vectors 473.

In this manner, for example, the method 300 can detect clinically-relevant divergence indicative of significant tissue deformation in the probed anatomic passageways and, likely, a change in position of the target anatomic structure from its determined location from the previously-obtained image data. Referring again to FIG. 3, at process 312, the method 300 identifies whether there is divergence. The method 300 may end at process 314 when no divergence is detected, or continue to process 316 when divergence is detected. It is understood that the method 300 can be repeated intermittently or continuously, such that identification of divergence is performed (at process 312) for a plurality of landmarks (e.g., for all or a subset of the carinas encountered by the medical instrument system as it is driven along the planned path), after the medical instrument system has traversed a specified distance; as the medical instrument system reaches the end of the planned path 452, as the medical instrument system approaches the target, etc.

To detect significant divergence, for example, some embodiments of the method 300 include a divergence classification technique that is implemented at process 312. For example, the divergence classification technique can classify (e.g., determine, predict, etc.) (i) the magnitude and/or direction of the divergence of a portion (e.g., anatomic passageways) of the anatomic region from a corresponding portion of the anatomic model and/or (ii) the magnitude and/or direction of the divergence of the actual location (e.g., real target location 435; FIGS. 4A and 4B) of a target from its virtual location (e.g., virtual target location 455; FIGS. 4A and 4B) within or relative to the anatomic model. The divergence classification technique may include finding one or more matching points between the planned path (e.g., virtual line of the airway) and the positional sensor data produced by the position sensor(s) of the medical instrument system, as discussed above. After determining the matching points, the technique may include calculating one or more divergence vectors, which can include vector(s) between one or more points along the planned path and corresponding positional sensor data point(s) (e.g., indicative of the position and/or shape of the elongated device 131), also discussed above. Notably, the technique may implement other ways to identify divergence of the positional sensor data from the pre-operative image data and/or other ways to update the location of the target, such as using simple translation of the end of the planned path onto one or more coordinate points corresponding to the distal region 138 of the elongated device 131 (FIG. 1). In the example divergence vector implementations, the determined divergence vectors may be different than those that use point-by-point vectorization of the planned path to the positional sensor data. For example, linear or quadratic interpolations can be used to determine the differences between the positional sensor data and the planned path. The divergence classification technique produces a quantitative value, referred to as a "divergence classifier," which can be a scalar or vector representation of the divergence of the anatomic region and/or of the target from the planned path (from their determined location in the previously-obtained image data) based on the divergence vectors calculated in accordance with some example embodiments of the process 310.

In some embodiments of the divergence classification technique, implemented at the process 312, the method 300 determines an offset between the portion of the virtual path and the position sensor data of the medical device, where the offset is a quantitative value that may correspond to an amount or degree of divergence between anatomic features determined from the previously-obtained image data and the same anatomic features probed by the insertable medical instrument while being driven along the planned path. In some implementations, the divergence classifier includes a device-to-path distance parameter, which includes a mean distance between at least one point on the planned path to the one or more position data points of the medical instrument system (e.g., at the location of the distal portion 138 of the elongate device 131), which can be determined using one or more divergence vectors calculated at process 310. The device-to-path distance parameter can be represented as x cm or other distance unit. In some embodiments, for example, the device-to-path distance parameter includes a range of mean distance values. Yet, in some implementations, the device-to-path distance parameter can include a mean distance among weighted divergence vectors. For example, as discussed above, divergence vectors closer to the target (e.g., at the distal end of the elongate device) may be weighted higher than divergence vectors further from the target.

Because the divergence classifier is a quantitative value, the divergence classifier can be applied to identify whether there is significant divergence of the target or other portion of the anatomic region probed by the medical instrument system. For example, if the device-to-path distance parameter is determined to be relatively small based on a divergence threshold, e.g., less than 1 mm, then the method 300 can determine there is no significant divergence at process 312 and terminate the method 300 (e.g., at least for this juncture of the medical procedure) at the process 314. Notably, the divergence threshold can vary for different anatomic regions or for different patients. In some examples for pulmonary airways, the divergence threshold to determine significant divergence of a target can be 1 cm or greater. Similarly, the divergence threshold can be a set of ranges, rather than a specific value, to inform of a degree of divergence. For example, the divergence threshold can include 0 mm to <5 mm in one range representing negligible divergence, 5 mm to <10 mm in a next range representing insignificant divergence, 10 mm to <20 mm in another range representing significant divergence, and so forth.

Also, for example, the divergence classifier can be used to determine if the user should be alerted to the divergence based on the amount or degree of the divergence. Moreover, for example, this feature may be used to derive metrics of divergence based on other clinical factors, or may be used as a signal to switch between different registration techniques for the medical device registration protocol.

In some embodiments, the method 300 may optionally include process 316. At process 316, the method 300 triggers a divergence alert when divergence is detected at 312. In some implementations of the process 316, the method 300 generates an alert when the divergence classifier exceeds a predetermined threshold. For example, in some implementations, the method 300 compares a predetermined divergence threshold of 1 cm or greater to the divergence classifier to trigger an alert to the user of the medical instrument system that the target anatomic structure 198 has significantly diverged from the planned path. FIGS. 5A and 5B, discussed in greater detail below, illustrate examples of alerting the user in example implementations of the process 316.

The method 300 may optionally include processes 318-322 directed to updating the anatomic model based on the comparison performed at the process 310 and/or on the divergence detected at the process 312. As shown in the flow diagram of FIG. 3, the method 300 identifies whether to update the anatomic model (e.g., a virtual image of the anatomic model and/or the target) at process 318. If the method 300 determines that updating the anatomic models is not warranted, the method 300 may end at block 320. Otherwise, the method 300 can proceed to implement process 322 to update the anatomic model by updating the depiction of a corresponding portion of the anatomic region, updating the planned path, and/or updating the virtual target position to a predicted position of the target (e.g., shown as predicted target location 445 in FIG. 4C, which is discussed in greater detail below). In some implementations, the process 318 may determine that updating the anatomic model is warranted based on the divergence classifier (e.g., when the identified divergence exceeds a specified threshold) or based on user input (e.g., provided via a display of the system, as discussed in greater detail below in connection with FIG. 5A). It is understood that the method 300 can be repeated intermittently or continuously, such that the determination whether to update the anatomic model is performed (at process 318) continuously or intermittently.

At process 322, the method 300 updates the anatomic model. In some implementations, this can include updating a corresponding portion of the anatomic region depicted in the anatomic model, updating the planned path projected onto the anatomic model, and/or updating the virtual target position 455 (FIGS. 4A-4C) to a predicted target location 445 (FIG. 4C) that is expected to better align with the target's actual or real target location 435 (FIGS. 4A-4C). For example, the method 300 may implement a technique to determine a predicted location of a target anatomic structure (e.g., a predicted real location), where the target has moved due to image-to-body divergence.

In some implementations, for example, the prediction technique finds matching points between the planned path (e.g., a virtual line or centerline of the anatomic passageway) and the position sensor data (e.g., shape data) produced by the sensor of the medical instrument system, as discussed in greater detail above. After determining the matching points, the technique calculates divergence vectors, which can include vector(s) between point(s) from the planned path to the one or more position data points associated with the shape of the medical instrument system. Notably, the technique may implement other ways to compare differences in the shape data to the previously-obtained image data and update the virtual target, such as using simple translation of the end of the planned path to the target onto the last piece of the catheter shape. In the divergence vector embodiments, the determined divergence vectors may be different than those that use point-by-point vectorization of the planned path to the medical instrument's shape. For example, linear or quadratic interpolations can be used to determine the differences in the position sensor data from the virtual planned path of the airways. The technique can update the virtual target position in real time as the user (e.g., physician) moves closer to the target tissue. Also, the virtual target position can be updated (e.g., by pushing a button or selection of a software tool) once the surgeon is close enough to the virtual target.

For example, in some embodiments of the method 300, the method further includes updating the virtual location of the target anatomic structure, which can include selecting data including a last one or more (n) vectors associated with points nearest to the target, fitting a curve to the selected data (wherein the curve includes a linear and quadratic), and extrapolating the curve to estimate a new target position of the anatomic structure in x,y,z coordinate points. Furthermore, in these and other embodiments, the updating the virtual location further includes applying a weighting value to one or more of the vectors.

FIG. 4C is a schematic diagram of the virtual navigation images of FIGS. 4A and 4B. As shown, the anatomic model 450 has been updated in FIG. 4C to align with the positional sensor data (e.g., the point cloud 260). In other words, the anatomic model 450 has been updated to illustrate deformation of anatomic passageways 152 local to the distal region of the medical instrument system. The planned path 452 has also been updated such that it better aligns with the positional sensor data. Furthermore, FIG. 4C illustrates a predicted target location 445 that represents an updated position of the virtual target location 455 of the target along a target divergence vector 463. The target divergence vector 463 is calculated using the plurality of divergence vectors 473 illustrated in FIG. 4B. For example, in some implementations, the target divergence vector 463 is calculated based on an average of all or subset of the divergence vectors 473 from FIG. 4B. For example, all or a subset of the divergence vectors 473 may be weighted in order to determine the target divergence vector 463. In some implementations, the weightings of divergence vectors 473 may be based on a distance between the end or tip of the elongate device 131 from the point of the divergence vector spanning from the elongate device 131, e.g., where divergence vectors closer to the end or tip are weighted greater. In these and other implementations, the weightings of the divergence vectors 473 may be based on a distance between the virtual target location 455 and a point of a corresponding divergence vector 473, e.g., where the divergence vectors closer to the virtual target location 455 are weighted heavier. Such distance-based weightings can be assigned in groups, e.g., based on distance, or individually weighted.

FIG. 5A is a schematic representation of an example display 510 illustrating a graphic user interface (GUI) having a GUI feature indicative of a divergence alert in accordance with various embodiments of the present technology. The display 510 can be produced by a display system (e.g., display system 610, discussed in greater detail in connection with FIG. 6) in communication with the medical instrument system (e.g., medical instrument system 604). As shown in FIG. 5A, the display 510 includes a real navigational image 570, a composite virtual navigational image 591 (also referred to as a "composite virtual image 591"), a virtual navigational image 592, and a divergence alert GUI feature 585.

The composite virtual image 591 of FIGS. 5A and 5B is displayed in the image reference frame (XI, YI, ZI) and includes an anatomic model 550 generated from image data of the anatomic region 150 (FIG. 1), e.g., captured by an imaging system. The anatomic model 550 is registered (i.e., dynamically referenced) with a point cloud of coordinate points (e.g., the point cloud 260 of FIG. 2) generated by the positional sensor system 608 (FIG. 1) to display a representation 504 within the anatomic model 550 of the tracked position, shape, pose, orientation, and/or movement of the medical instrument system 604 (e.g., of the elongate device 131) within the patient (FIG. 1). In FIG. 5A, the anatomic model 550 of the imaged anatomic region 150 of the patient includes the target 198 as determined from the pre-operative images shown with respect to virtual anatomic passageways 552 spanning from bronchial tubes 557 to deep passageways 558. In FIG. 5B, the anatomic model 550 of the imaged anatomic region 150 of the patient includes an updated target 598 as determined from implementation of the process 322, also shown with respect to virtual anatomic passageways 552 spanning from bronchial tubes 557 to deep passageways 558.

The divergence alert GUI feature 585 is shown in FIG. 5A on the display 510 proximate the composite virtual image 591, which for example, can be implemented as an icon, dialog box, or other manifestations that indicate the identification of divergence in accordance with processes 312-316 described above with reference to FIG. 3. In the particular example shown in FIG. 5A, the divergence alert GUI feature 585 (optionally) includes an updated registration prompt, allowing a user to indicate whether they want the system to update the registration of the medical instrument system in accordance with the process 318-322. The user can select (a) interactive GUI feature 587*a* to update the registration (e.g., of the target anatomic feature 198 and/or the planned path in the display 510) or (b) interactive GUI feature 587*b* to not update the registration.

FIG. 5B is a schematic representation of the example display 510 of FIG. 5A, but illustrating the display after the user selects interactive GUI feature 587*a*, which is indicative of an affirmative command to update the registration of anatomic model to the position sensor data, the location of the target 198, and/or the planned path in the display 510 (e.g., at least in the composite virtual navigational image 591).

Referring to both FIGS. 5A and 5B together, the real navigational image 570 illustrates real patient anatomy (e.g., a carina 571 marking a branching point of two anatomic passageways 152) from a viewpoint oriented distally away from the distal portion 138 of the elongate device 131 (FIG. 1). For example, the real navigational image 570 can be captured by the one or more image capture devices 747 (e.g., embodiments of endoscopic imaging system 609, discussed in greater detail in connection with FIG. 6) and provided to the display system 610 to be presented on the display 510 in real-time or near real-time.

Figure 6:
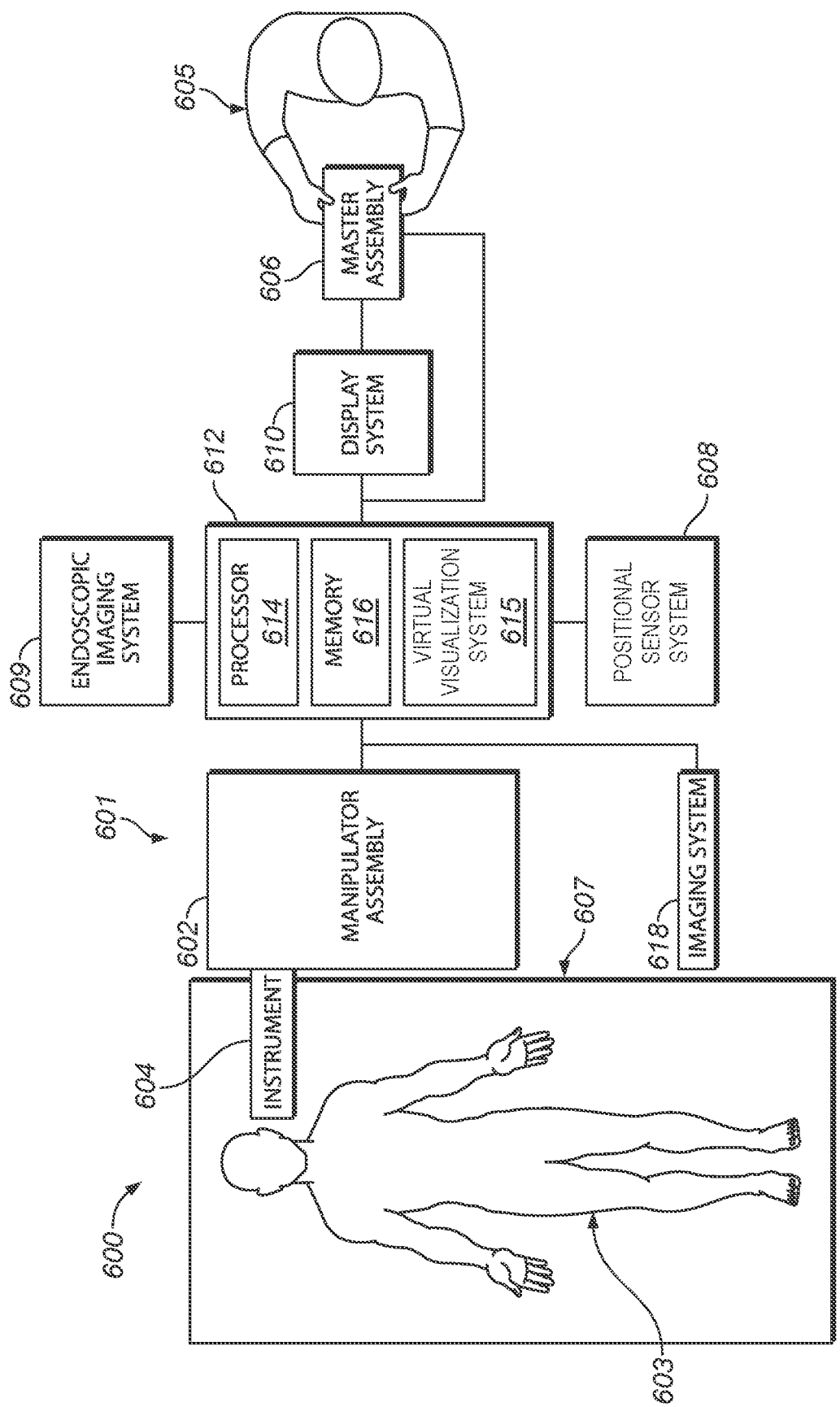
FIG. 6 is a schematic representation of a robotic or teleoperated medical system configured in accordance with various embodiments of the present technology.

In some embodiments, the composite virtual image 591 is generated by a virtual visualization system (e.g., virtual visualization system 615, discussed in greater detail in connection with FIG. 6) of the control system 612 (FIG. 6). Generating the composite virtual image 591 can involve registering the image reference frame (XI, YI, ZI) with the surgical reference frame (XS, YS, ZS) and/or to the medical instrument reference frame (XM, YM, ZM). For example, this registration may rotate, translate, or otherwise manipulate by rigid and/or non-rigid transforms coordinate points of the point cloud (e.g., the coordinate points 262 of the point cloud 260 of FIG. 2) captured by the positional sensor system 608 to align the coordinate points with the anatomic model 550. The registration between the image and surgical/ instrument frames of reference may be achieved, for example, by using an ICP technique, or another point cloud registration technique.

As further shown in FIGS. 5A and 5B, the virtual navigational image 592 illustrates virtual patient anatomy, such as a virtual carina 501 (corresponding to the real carina 571) marking a branching point of two virtual anatomic passageways 552 (corresponding to real anatomic passageways 152) of the anatomic model 550, from substantially the same location at which the real navigational image 570 is captured by the image capture device 747 (FIG. 1). Thus, the virtual navigational image 592 provides a rendered estimation of patient anatomy visible to the image capture device 747 at a given location within the anatomic region 150. Because the virtual navigational image 592 is based, at least in part, on the registration of a point cloud generated by the positional sensor system 608 and image data captured by the imaging system 618 (FIG. 1), the correspondence between the virtual navigational image 592 and the real navigational image 570 provides insight regarding the accuracy of the registration.

As further shown in FIGS. 5A and 5B, the virtual navigational image 592 can optionally include a navigation path overlay 599 (e.g., a planned path). In some embodiments, the navigation path overlay 599 is used to aid an operator to navigate the medical instrument system 604 through anatomic passageways of an anatomic region 150 to the target anatomic structure 198 within the patient. For example, the navigation path overlay 599 can illustrate a "best" path through an anatomic region for an operator to follow to deliver the distal portion of the elongated device 132 to a target location within the patient. In some embodiments, the navigation path overlay 599 can be aligned with a centerline of or another line along (e.g., the floor of) a corresponding anatomic passageway.

B. EMBODIMENTS OF ROBOTIC OR TELEOPERATED MEDICAL SYSTEMS FOR IMPLEMENTING IMAGE-TO-BODY DIVERGENCE IDENTIFICATION AND MITIGATION TECHNIQUES DURING A MEDICAL PROCEDURE

FIG. 6 is a schematic representation of a robotic or teleoperated medical system 600 ("medical system 600") configured in accordance with various embodiments of the present technology. As shown, the medical system 600 includes a manipulator assembly 602, the medical instrument system 604 (from FIG. 1), a master assembly 606, and a control system 612. The manipulator assembly 602 supports the medical instrument system 604 and drives the medical instrument system 604 at the direction of the master assembly 606 and/or the control system 612 to perform various medical procedures on a patient 603 positioned on a table 607 in a surgical environment 601. In this regard, the master assembly 606 generally includes one or more control devices that can be operated by an operator 605 (e.g., a physician) to control the manipulator assembly 602. Additionally, or alternatively, the control system 612 includes a computer processor 614 and at least one memory 616 for effecting control between the medical instrument system 604, the master assembly 606, and/or other components of the medical system 600. The control system 612 can also include programmed instructions (e.g., a non-transitory computer-readable medium storing the instructions) to implement any one or more of the methods described herein, including instructions for providing information to a display system 610 and/or processing data for registration of the medical instrument system 604 with the anatomical model of the patient 603 (as previously described above). The manipulator assembly 602 can be a teleoperated, a non-teleoperated, or a hybrid teleoperated and non-teleoperated assembly. Thus, all or a portion of the master assembly 606 and/or all or a portion of the control system 612 can be positioned inside or outside of the surgical environment 601.

To aid the operator 605 in controlling the manipulator assembly 602 and/or the medical instrument system 604 during an image-guided medical procedure, the medical system 600 may further include a positional sensor system 608, an endoscopic imaging system 609, an imaging system 618, and/or a virtual visualization system 615. In some embodiments, the positional sensor system 608 includes a location sensor system (e.g., an electromagnetic (EM) sensor system) and/or a shape sensor system for capturing positional sensor data (e.g., position, orientation, speed, velocity, pose, shape, etc.) of the medical instrument system 604. In these and other embodiments, the endoscopic imaging system 609 includes one or more image capture devices (not shown) that record endoscopic image data that includes concurrent or real-time images (e.g., video, still images, etc.) of patient anatomy. Images captured by the endoscopic imaging system 609 may be, for example, two or three-dimensional images of patient anatomy captured by an image capture device positioned within the patient 603, and are referred to as "real navigational images," such as the real navigation images 570 shown in FIGS. 5A and 5B.

In some embodiments, the medical instrument system 604 may include components of the positional sensor system 608 and/or components of the endoscopic imaging system 609. For example, components of the positional sensor system 608 and/or components of the endoscopic imaging system 609 can be integrally or removably coupled to the medical instrument system 604. Additionally, or alternatively, the endoscopic imaging system 609 can include a separate endoscope (not shown) attached to a separate manipulator assembly (not shown) that can be used in conjunction with the medical instrument system 604 to image patient anatomy. The positional sensor system 608 and/or the endoscopic imaging system 609 may be implemented as hardware, firmware, software, or a combination thereof that interact with or are otherwise executed by one or more computer processors, such as the computer processor(s) 614 of the control system 612.

The imaging system 618 of the medical system 600 may be arranged in the surgical environment 601 near the patient 603 to obtain real-time and/or near real-time images of the patient 603 before, during, and/or after a medical procedure. In some embodiments, the imaging system 618 includes a mobile C-arm cone-beam computerized tomography (CT) imaging system for generating three-dimensional images. For example, the imaging system 618 can include a DynaCT imaging system from Siemens Corporation, or another suitable imaging system. In these and other embodiments, the imaging system 618 can include other imaging technologies, including magnetic resonance imaging (MM), fluoroscopy, thermography, ultrasound, optical coherence tomography (OCT), thermal imaging, impedance imaging, laser imaging, nanotube X-ray imaging, and/or the like.

The virtual visualization system 615 of the control system 612 provides navigation and/or anatomy-interaction assistance to the operator 605 when controlling the medical instrument system 604 during an image-guided medical procedure. As described in greater detail below, virtual navigation using the virtual visualization system 615 can be based, at least in part, upon reference to an acquired pre-operative or intra-operative dataset (e.g., based, at least in part, upon reference to data generated by the positional sensor system 608, the endoscopic imaging system 609, and/or the imaging system 618) of anatomic passageways of the patient 603. In some implementations, for example, the virtual visualization system 615 processes pre-operative and/or intraoperative image data of an anatomic region of the patient 603 captured by the imaging system 618 to generate an anatomic model (not shown) of the anatomic region. The virtual visualization system 615 then registers the anatomic model to positional sensor data generated by the positional sensor system 608 and/or to endoscopic image data generated by the endoscopic imaging system 609 to (i) map the tracked position, orientation, pose, shape, and/or movement of the medical instrument system 604 within the anatomic region to a correct position within the anatomic model, and/or (ii) determine a virtual navigational image of virtual patient anatomy of the anatomic region from a viewpoint of the medical instrument system 604 at a location within the anatomic model corresponding to a location of the medical instrument system 604 within the patient 603.

The display system 610 can display various images or representations of patient anatomy and/or of the medical instrument system 604 that are generated by the positional sensor system 608, by the endoscopic imaging system 609, by the imaging system 618, and/or by the virtual visualization system 615. In some embodiments, the display system 610 and/or the master assembly 606 may be oriented so the operator 605 can control the manipulator assembly 602, the medical instrument system 604, the master assembly 606, and/or the control system 612 with the perception of telepresence.

As discussed above, the manipulator assembly 602 drives the medical instrument system 604 at the direction of the master assembly 606 and/or the control system 612. In this regard, the manipulator assembly 602 can include select degrees of freedom of motion that may be motorized and/or teleoperated and select degrees of freedom of motion that may be non-motorized and/or non-teleoperated. For example, the manipulator assembly 602 can include a plurality of actuators or motors (not shown) that drive inputs on the medical instrument system 604 in response to commands received from the control system 612. The actuators can include drive systems (not shown) that, when coupled to the medical instrument system 604, can advance the medical instrument system 604 into a naturally or surgically created anatomic orifice. Other drive systems may move a distal portion (not shown) of the medical instrument system 604 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, or alternatively, the actuators can be used to actuate an articulable end effector of the medical instrument system 604 (e.g., for grasping tissue in the jaws of a biopsy device and/or the like).

Figure 7:
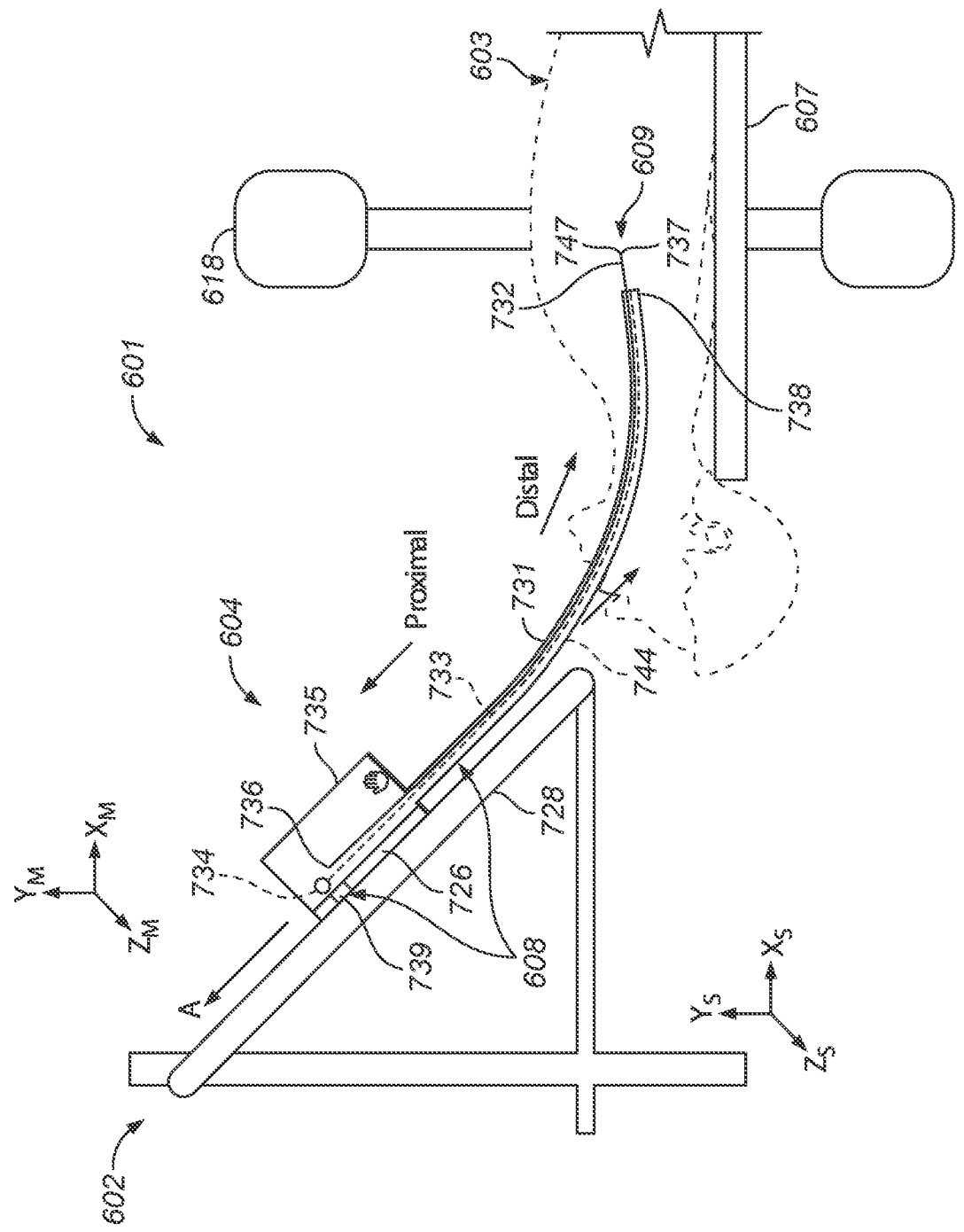
FIG. 7 is a schematic representation of a manipulator assembly, a medical instrument system, and an imaging system configured in accordance with various embodiments of the present technology.

FIG. 7 is a schematic representation of the manipulator assembly 602, the medical instrument system 604, and the imaging system 618 of FIG. 6 within the surgical environment 601 and configured in accordance with various embodiments of the present technology. As shown in FIG. 7, the surgical environment 601 has a surgical frame of reference (XS, YS, ZS) in which the patient 603 is positioned on the table 607, and the medical instrument system 604 has a medical instrument frame of reference (XM, YM, ZM) within the surgical environment 601. During the medical procedure, the patient 603 may be stationary within the surgical environment 601 in the sense that gross patient movement can be limited by sedation, restraint, and/or other means. In these and other embodiments, cyclic anatomic motion of the patient 603, including respiration and cardiac motion, may continue unless the patient 603 is asked to hold his or her breath to temporarily suspend respiratory motion.

The manipulator assembly 602 includes an instrument carriage 726 mounted to an insertion stage 728. In the illustrated embodiment, the insertion stage 728 is linear, while in other embodiments, the insertion stage 728 is curved or has a combination of curved and linear sections. In some embodiments, the insertion stage 728 is fixed within the surgical environment 601. Alternatively, the insertion stage 728 can be movable within the surgical environment 601 but have a known location (e.g., via a tracking sensor (not shown) or other tracking device) within the surgical environment 601. In these alternatives, the medical instrument frame of reference (XM, YM, ZM) is fixed or otherwise known relative to the surgical frame of reference (XS, YS, ZS).

The medical instrument system 604 of FIG. 7 includes an elongate device 731 (e.g., corresponding to elongated device 131 in FIG. 1), a medical instrument 732, an instrument body 735, at least a portion of the positional sensor system 608, and at least a portion of the endoscopic imaging system 609. In some embodiments, the elongate device 731 is a flexible catheter or other biomedical device that defines a channel or lumen 744. The channel 744 can be sized and shaped to receive the medical instrument 732 (e.g., via a proximal end 736 of the elongate device 731 and/or an instrument port (not shown)) and facilitate delivery of the medical instrument 732 to a distal portion 738 of the elongate device 731. The elongate device 731 is coupled to the instrument body 735, which in turn is coupled and fixed relative to the instrument carriage 726 of the manipulator assembly 602.

In operation, the manipulator assembly 602 can control insertion motion (e.g., proximal and/or distal motion along an axis A) of the elongate device 731 into the patient 603 via a natural or surgically created anatomic orifice of the patient 603 to facilitate navigation of the elongate device 731 through anatomic passageways of an anatomic region of the patient 603 and/or to facilitate delivery of a distal portion 738 of the elongate device 731 to or near a target location within the patient 603. For example, the instrument carriage 726 and/or the insertion stage 728 may include actuators (not shown), such as servomotors, that facilitate control over motion of the instrument carriage 726 along the insertion stage 728. Additionally, or alternatively, the manipulator assembly 602 in some embodiments can control motion of the distal portion 738 of the elongate device 731 in multiple directions, including yaw, pitch, and roll rotational directions (e.g., to navigate patient anatomy). To this end, the elongate device 731 may house or include cables, linkages, and/or other steering controls (not shown) that the manipulator assembly 602 can use to controllably bend the distal portion 738 of the elongate device 731. For example, the elongate device 731 can house at least four cables that can be used by the manipulator assembly 602 to provide (i) independent "up-down" steering to control a pitch of the distal portion 738 of the elongate device 731 and (ii) independent "left-right" steering of the elongate device 731 to control a yaw of the distal portion 738 of the elongate device 731.

The medical instrument 732 of the medical instrument system 604 can be used for medical procedures, such as for survey of anatomic passageways, surgery, biopsy, ablation, illumination, irrigation, and/or suction. Thus, the medical instrument 732 can include image capture probes, biopsy instruments, laser ablation fibers, and/or other surgical, diagnostic, and/or therapeutic tools. For example, the medical instrument 732 can include an endoscope or other biomedical device having the one or more image capture devices 747 positioned at a distal portion 737 of and/or at other locations along the medical instrument 732. In these embodiments, an image capture device 747 can capture one or more real navigational images or video (e.g., a sequence of one or more real navigational image frames) of anatomic passageways and/or other real patient anatomy while the medical instrument 732 is within an anatomic region of the patient 603.

As discussed above, the medical instrument 732 can be deployed into and/or be delivered to a target location within the patient 603 via the channel 744 defined by the elongate device 731. In embodiments in which the medical instrument 732 includes an endoscope or other biomedical device having an image capture device 747 at its distal portion 737, the image capture device 747 can be advanced to the distal portion 738 of the elongate device 731 before, during, and/or after the manipulator assembly 602 navigates the distal portion 738 of the elongate device 731 to a target location within the patient 603. In these embodiments, the medical instrument 732 can be used as a survey instrument to capture real navigational images of anatomic passageways and/or other real patient anatomy, and/or to aid an operator (not shown) to navigate the distal portion 738 of the elongate device 731 through anatomic passageways to the target location.

As another example, after the manipulator assembly 602 positions the distal portion 738 of the elongate device 731 proximate a target location within the patient 603, the medical instrument 732 can be advanced beyond the distal portion 738 of the elongate device 731 to perform a medical procedure at the target location. Continuing with this example, after all or a portion of the medical procedure at the target location is complete, the medical instrument 732 can be retracted back into the elongate device 731 and, additionally or alternatively, be removed from the proximal end 736 of the elongate device 731 or from another instrument port (not shown) along the elongate device 731.

As shown in FIG. 7, the positional sensor system 608 of the medical instrument system 604 includes a shape sensor 733 and a position measuring device 739. In these and other embodiments, the positional sensor system 608 can include other position sensors (e.g., accelerometers, rotary encoders, etc.) in addition to or in lieu of the shape sensor 733 and/or the position measuring device 739.

The shape sensor 733 of the positional sensor system 608 includes an optical fiber extending within and aligned with the elongate device 731. In one embodiment, the optical fiber of the shape sensor 733 has a diameter of approximately 200 μm. In other embodiments, the diameter of the optical fiber may be larger or smaller. The optical fiber of the shape sensor 733 forms a fiber optic bend sensor that is used to determine a shape, orientation, and/or pose of the elongate device 731. In some embodiments, optical fibers having Fiber Bragg Gratings (FBGs) can be used to provide strain measurements in structures in one or more dimensions. Various systems and methods for monitoring the shape and relative position of an optical fiber in three dimensions are described in further detail in U.S. Patent Application Publication No. 2006/0013523 (filed Jul. 13, 2005) (disclosing fiber optic position and shape sensing device and method relating thereto); U.S. Pat. No. 7,781,724 (filed on Sep. 26, 2006) (disclosing fiber-optic position and shape sensing device and method relating thereto); U.S. Pat. No. 7,772,541 (filed on Mar. 12, 2008) (disclosing fiber-optic position and/or shape sensing based on Rayleigh scatter); and U.S. Pat. No. 6,389,187 (filed on Jun. 17, 1998) (disclosing optical fiber bend sensors), which are all incorporated by reference herein in their entireties. In these and other embodiments, sensors of the present technology may employ other suitable strain sensing techniques, such as Rayleigh scattering, Raman scattering, Brillouin scattering, and Fluorescence scattering. In these and still other embodiments, the shape of the elongate device 731 may be determined using other techniques. For example, a history of the pose of the distal portion 738 of the elongate device 731 can be used to reconstruct the shape of elongate device 731 over an interval of time.

In some embodiments, the shape sensor 733 is fixed at a proximal point 734 on the instrument body 735 of the medical instrument system 604. In operation, for example, the shape sensor 733 measures a shape in the medical instrument reference frame (XM, YM, ZM) from the proximal point 734 to another point along the optical fiber, such as the distal portion 738 of the elongate device 731. The proximal point 734 of the shape sensor 733 may be movable along with instrument body 735 but the location of proximal point 734 may be known (e.g., via a tracking sensor (not shown) or other tracking device).

The position measuring device 739 of the positional sensor system 608 provides information about the position of the instrument body 735 as it moves along the insertion axis A on the insertion stage 728 of the manipulator assembly 602. In some embodiments, the position measuring device 739 includes resolvers, encoders, potentiometers, and/or other sensors that determine the rotation and/or orientation of actuators (not shown) controlling the motion of the instrument carriage 726 of the manipulator assembly 602 and, consequently, the motion of the instrument body 735 of the medical instrument system 604.

C. EXAMPLES

Several aspects of the present technology are set forth in the following examples. Although several aspects of the present technology are set forth in examples directed to systems, computer-readable mediums, and methods, any of these aspects of the present technology can similarly be set forth in examples directed to any of systems, computer-readable mediums, and methods in other embodiments.

1. A system for determining divergence of an anatomic region from an anatomic model of the anatomic region, the system comprising: a medical device comprising a sensor, wherein the medical device is insertable within a patient; and a computing device in communication with the medical device, the computing device comprising a processor, and a memory coupled to the processor and storing instructions that, when executed by the processor, cause the system to perform operations comprising: receiving sensor data acquired by the sensor of the medical device while the medical device is inserted within an anatomic region of the patient and after the medical device has been registered to an anatomic model of the anatomic region, wherein the anatomic model is based on previously-obtained image data of the anatomic region and includes a virtual path extending throughout the anatomic model to an anatomic structure of interest, and wherein the sensor data indicates a location of at least a portion of the medical device, comparing the sensor data to a corresponding portion of the virtual path, based at least in part on the comparing, producing a divergence classifier indicative of a divergence of the anatomic region from the anatomic model, and generating an alert when the divergence classifier exceeds a predetermined threshold.

2. The system of example 1 wherein the generating the alert includes displaying a graphical user interface on a display in communication with the computing device, wherein the graphical user interface includes one or both of graphical and text information indicative of a determination of the divergence of the anatomic region from the anatomic model.

3. The system of example 2 wherein the graphical user interface includes a prompt to command the system to update a location of the anatomic region within the anatomic model.

4. The system of any one of examples 1-3 wherein the operations further comprise updating a virtual location of the anatomic region with respect to the anatomic model while the medical device is within the anatomic region.

5. The system of example 4 wherein the produced divergence classifier is indicative of a divergence of the anatomic structure of interest from the anatomic model, and wherein the operations further comprise updating a virtual location of the anatomic structure of interest while the medical device is within the anatomic region.

6. The system of example 5 wherein the updating the virtual location of the anatomic structure includes: calculating one or more divergence vectors between the corresponding portion of the virtual path and the at least a portion of the medical device, selecting one or more of the divergence vectors associated with one or more positional points located along the at least a portion of the medical device that are nearest to the anatomic structure, fitting a curve to the selected one or more divergence vectors, and extrapolating the curve to estimate a new target position of the anatomic structure in x,y,z coordinate points.

7. The system of example 6 wherein the updating the virtual location of the anatomic structure further includes applying a weighting value to at least one of the one or more divergence vectors.

8. The system of any one of examples 1-7 wherein comparing includes:
determining an offset between the corresponding portion of the virtual path and the medical device.

9. The system of example 8 wherein determining the offset includes generating one or more divergence vectors pointing from the corresponding portion of the virtual path to the medical device, and wherein the one or more divergence vectors are point matched.

10. The system of any one of examples 1-9 wherein the operations further comprise analyzing the sensor data to determine a shape of the at least a portion of the medical device.

11. The system of example 10, wherein comparing the sensor data to the corresponding portion of the virtual path includes comparing the shape of the at least a portion of the medical device with a portion of the virtual path.

12. The system of example 11 wherein the anatomic region includes an anatomic passageway, and wherein the determining the offset includes measuring a magnitude and a direction of the anatomic passageway deformation to determine a plurality of deformation vectors, and comparing the shape of the at least a portion of the medical device in real time to the virtual path of the anatomic passageways predetermined from the previously-obtained image data based on the deformation vectors.

13. The system of any one of examples 1-12 wherein the divergence classifier includes a device-to-path distance parameter that includes a mean distance between a last region of the portion of the virtual path to a distal end portion of the medical device.

14. The system of any one of examples 1-13 wherein the sensor data acquired by the sensor of the medical device are associated with one or more of a position, orientation, speed, pose, and/or shape of the medical device.

15. The system of any one of examples 1-14 wherein the medical device includes a catheter, and wherein the sensor includes a shape sensor comprising an optical fiber extending within and aligned with an elongate portion of the catheter.

16. The system of example 15 wherein a plurality of points associated with the shape of the medical device are determined from sampled points by the shape sensor.

17. The system of any one of examples 1-16 wherein the medical device includes a catheter, and wherein the sensor includes an electromagnetic (EM) sensor located at a distal end or tip of the catheter.

18. The system of example 17 wherein the plurality of points associated with the shape of the medical device are determined from a plurality of individual points measured at the distal end or tip of the catheter by the EM sensor as it is driven through an anatomic passageway.

19. The system of any one of examples 1-18 wherein the sensor of the medical device is configured to generate one or both of position sensor data and motion sensor data during data sampling of the anatomic region of the patient, and wherein the operations further comprise:
identifying an anatomical landmark of the anatomic region while the medical device is navigating within the anatomic region of the patient, implementing the comparing step to compare the sensor data to the corresponding portion of the virtual path associated with the anatomical landmark, and updating registration of the medical device based, at least in part, on the compared sensor data to the anatomical landmark.

20. A non-transitory, computer-readable medium storing instructions thereon that, when executed by one or more processors of a computing system, cause the computing system to perform operations comprising:
receiving sensor data acquired by a sensor of a medical device while the medical device is inserted within an anatomic region of a patient and after the medical device has been registered to an anatomic model of the anatomic region, wherein the anatomic model is based on previously-obtained image data of the anatomic region and includes a virtual path extending throughout the anatomic model to an anatomic structure of interest, and wherein the sensor data indicates a location of at least a portion of the medical device, comparing the sensor data to a corresponding portion of the virtual path, based at least in part on the comparing, producing a divergence classifier indicative of a divergence of the anatomic region from the anatomic model, and

D. CONCLUSION

The systems and methods described herein can be provided in the form of tangible and non-transitory machinereadable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Although many of the embodiments are described above in the context of navigating and performing medical procedures within lungs of a patient, other applications and other embodiments in addition to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, GI system, and/or heart of a patient.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. Additionally, or alternatively, the term "patient" should be considered to include human and/or non-human (e.g., animal) patients upon which a medical procedure is being performed.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. A system for determining divergence of an anatomic region from an anatomic model of the anatomic region, the system comprising:
   a medical device comprising a sensor, wherein the medical device is insertable within a patient; and
   a computing device in communication with the medical device, the computing device comprising a processor, and a memory coupled to the processor and storing instructions that, when executed by the processor, cause the system to perform operations comprising:
receiving sensor data acquired by the sensor of the medical device while the medical device is inserted within an anatomic region of the patient and after the medical device has been registered to an anatomic model of the anatomic region, wherein the anatomic model is based on previously-obtained image data of the anatomic region and includes a virtual path extending throughout the anatomic model to an anatomic structure of interest, and wherein the sensor data indicates a location of at least a portion of the medical device,
comparing the sensor data to a corresponding portion of the virtual path,
based at least in part on the comparing, producing a divergence classifier indicative of a divergence of the anatomic region from the anatomic model, wherein the divergence classifier is produced based on one or more weighted divergence vectors, and
generating an alert when the divergence classifier exceeds a predetermined threshold.

2. The system of claim 1 wherein the generating the alert includes displaying a graphical user interface on a display in communication with the computing device, wherein the graphical user interface includes one or both of graphical and text information indicative of a determination of the divergence of the anatomic region from the anatomic model.

3. The system of claim 2 wherein the graphical user interface includes a prompt to command the system to update a location of the anatomic region within the anatomic model.

4. The system of claim 1 wherein the operations further comprise updating a virtual location of the anatomic region with respect to the anatomic model while the medical device is within the anatomic region.

5. The system of claim 4 wherein the produced divergence classifier is indicative of a divergence of the anatomic structure of interest from the anatomic model, and wherein the operations further comprise updating a virtual location of the anatomic structure of interest while the medical device is within the anatomic region.

6. The system of claim 5 wherein the updating the virtual location of the anatomic structure includes:
calculating one or more divergence vectors between the corresponding portion of the virtual path and the at least a portion of the medical device,
selecting one or more of the divergence vectors associated with one or more positional points located along the at least a portion of the medical device that are nearest to the anatomic structure,
fitting a curve to the selected one or more divergence vectors, and
extrapolating the curve to estimate a new target position of the anatomic structure in x,y,z coordinate points.

7. The system of claim 6 wherein the updating the virtual location of the anatomic structure further includes applying a weighting value to at least one of the one or more divergence vectors to produce the one or more weighted divergence vectors.

8. The system of claim 1 wherein comparing includes:
determining an offset between the corresponding portion of the virtual path and the medical device.

9. The system of claim 8 wherein determining the offset includes generating one or more divergence vectors pointing from the corresponding portion of the virtual path to the medical device, and wherein the one or more divergence vectors are point matched.

10. The system of claim 1 wherein the operations further comprise analyzing the sensor data to determine a shape of the at least a portion of the medical device.

11. The system of claim 10, wherein comparing the sensor data to the corresponding portion of the virtual path includes comparing the shape of the at least a portion of the medical device with a portion of the virtual path.

12. The system of claim 11 wherein the anatomic region includes an anatomic passageway, and wherein comparing the sensor data to the corresponding portion of the virtual path further includes determining an offset between the corresponding portion of the virtual path and the medical device, and wherein determining the offset includes measuring a magnitude and a direction of anatomic passageway deformation to determine a plurality of divergence vectors and comparing the shape of the at least a portion of the medical device in real time to the virtual path of the anatomic passageways predetermined from the previously-obtained image data based on the divergence vectors.

13. The system of claim 1 wherein the divergence classifier includes a device-to-path distance parameter that includes a mean distance between a last region of the portion of the virtual path to a distal end portion of the medical device.

14. The system of claim 1 wherein the sensor data acquired by the sensor of the medical device are associated with one or more of a position, orientation, speed, pose, and/or shape of the medical device.

15. The system of claim 1 wherein the medical device includes a catheter, and wherein the sensor includes a shape sensor comprising an optical fiber extending within and aligned with an elongate portion of the catheter.

16. The system of claim 15 wherein a plurality of points associated with a shape of the medical device are determined from sampled points by the shape sensor.

17. The system of claim 1 wherein the medical device includes a catheter, and wherein the sensor includes an electromagnetic (EM) sensor located at a distal end or tip of the catheter.

18. The system of claim 17 wherein a plurality of points associated with a shape of the medical device are determined from a plurality of individual points measured at the distal end or tip of the catheter by the EM sensor as it is driven through an anatomic passageway.

19. The system of claim 1 wherein the sensor of the medical device is configured to generate one or both of position sensor data and motion sensor data during data sampling of the anatomic region of the patient, and wherein the operations further comprise:
identifying an anatomical landmark of the anatomic region while the medical device is navigating within the anatomic region of the patient,
implementing the comparing step to compare the sensor data to the corresponding portion of the virtual path associated with the anatomical landmark, and
updating registration of the medical device based, at least in part, on the compared sensor data to the anatomical landmark.

20. A non-transitory, computer-readable medium storing instructions thereon that, when executed by one or more processors of a computing system, cause the computing system to perform operations comprising:
receiving sensor data acquired by a sensor of a medical device while the medical device is inserted within an anatomic region of a patient and after the medical device has been registered to an anatomic model of the anatomic region, wherein the anatomic model is based on previously-obtained image data of the anatomic region and includes a virtual path extending throughout the anatomic model to an anatomic structure of interest, and wherein the sensor data indicates a location of at least a portion of the medical device, comparing the sensor data to a corresponding portion of the virtual path, based at least in part on the comparing, producing a divergence classifier indicative of a divergence of the anatomic region from the anatomic model, wherein the divergence classifier is produced based on one or more weighted divergence vectors, and generating an alert when the divergence classifier exceeds a predetermined threshold.

* * * * *

UNITED STATES PATENT AND TRADEMARK OFFICE
CERTIFICATE OF CORRECTION

| | | |
|---|---|---|
| PATENT NO. | : 12,349,980 B2 | Page 1 of 1 |
| APPLICATION NO. | : 18/041373 | |
| DATED | : July 8, 2025 | |
| INVENTOR(S) | : Leah Muller, Paris A. Hajali, Jr. and Hui Zhang | |

It is certified that error appears in the above-identified patent and that said Letters Patent is hereby corrected as shown below:

In the Specification

Column 20, Line 57, change "(MM)" to -- (MRI) --

Signed and Sealed this
Twelfth Day of August, 2025

Coke Morgan Stewart
*Acting Director of the United States Patent and Trademark Office*